United States Patent [19]

Goldberg

[11] Patent Number: 5,340,736
[45] Date of Patent: Aug. 23, 1994

[54] ATP-DEPENDENT PROTEASE AND USE OF INHIBITORS FOR SAME IN THE TREATMENT OF CACHEXIA AND MUSCLE WASTING

[75] Inventor: Alfred L. Goldberg, Brookline, Mass.

[73] Assignee: The President & Fellows of Harvard College, Cambridge, Mass.

[21] Appl. No.: 699,184

[22] Filed: May 13, 1991

[51] Int. Cl.$^5$ ............................................. C12N 9/64
[52] U.S. Cl. ........................................ 435/226; 435/219
[58] Field of Search .............................. 435/219, 226

[56] References Cited

FOREIGN PATENT DOCUMENTS

PCT/US92/-
  03914 11/1992 PCT Int'l Appl. .

OTHER PUBLICATIONS

Dahlmann et al., Biochimica Et Biophysica Acta, 991:253–262, (1989).
Kuehn et al. Biochimica Et Biophysica Acta. 991:263–271, (1989).
Nai–En et al., Biological Abstracts.–Microfilms; Abstr. Nr. 98518; 87: (1989) & Comp. Biochem. Physiol. 91:777–782, (1988).
Okada et al., Biochimica Et Biophysica Acta, 1073:514–520, (1991).
Fagan et al., Biochemical Journal, 243:335–343, (1987).
Reckelhoff et al., FASEB Journal; A1409: Abstr. Nr. 6028; 5: (1991) and 75th Annual Meeting of the Federation of American Societies for Experimental Biology, Atlanta Ga. Apr. 21-25, 1991.
Mattews et al., Proceedings of the National Academy of Sciences of USA 86:2597–2601, (1989).
Murakami et al., Proceedings of the National Academy of Sciences of USA 83:7588–7592, (1986).
Chu–Ping et al., Biological Abstracts–Microfilms; Abstr. NR, 130496; 93:(1992) and Biochimica Et Biophysica ACTA 1119:303–311, (1992).
Furuno, K. et al., J. Biol. Chem., 265:8550–8557 (1990).
Driscoll, Jr. and A. L. Goldberg, J. Biol. Chem. 265:4789–4792 (1990).
Ciechanover et al., TIBS, 14:483–488 (1989).
Ganoth et al., J. Biol. Chem., 263:12412–12419 (1988).
Han et al., FASEB Abstract, 1558 (1988).
Lowell et al., Biochem. J. 234: 237–240 (1986).
Fagan et al., J. Biol. Chem. 261 (13): 5705–5713 (May 5, 1986).
Hershko et al., J. Biol. Chem., 257 (23): 13964–13970 (Dec. 10, 1982).
Etlinger et al., Proc. Natl. Acad. Sci., 74 (1):54–58 (Jan. 1977).

*Primary Examiner*—Charles L. Patterson, Jr.
*Attorney, Agent, or Firm*—Sterne, Kessler, Goldstein & Fox

[57] ABSTRACT

The ATP-ubiquitin-dependent process has been shown to be responsible for the excessive protein degradation which occurs in conditions or disease states in which there is severe loss of body mass and negative nitrogen balance has been identified and key constituents in the process identified. A method of inhibiting the accelerated or enhanced proteolysis, a method of identifying inhibitors of the process, multipain and the proteasome inhibitor are the subject of the claimed invention.

2 Claims, 12 Drawing Sheets

ATP-DEPENDENT PROTEASE AND USE OF INHIBITORS FOR SAME IN THE TREATMENT OF CACHEXIA AND MUSCLE WASTING

FUNDING

Work leading to this invention was supported by the National Institutes of Health and The Muscular Dystrophy Association.

BACKGROUND OF THE INVENTION

Mammalian cells contain at least four proteolytic systems which appear to serve distinct functions in the turnover of cell proteins. In the cytosol, there is a soluble proteolytic pathway that requires ATP and involves the polypeptide ubiquitin (Ub). This multicomponent system catalyzes the selective degradation of highly abnormal proteins and short-lived regulatory proteins. However, this process also appears to be responsible for the breakdown of most proteins in maturing reticulocytes. Boches, F. and A. L. Goldberg, *Science*, 215: 978-980 (1982); Spenser, S. and J. Etlinger, *J. Biol. Chem.*, 257:14122-14127 (1985)) and in growing fibroblasts (Ciechanover, A. et al., *Cell*, 37:57-66 (1984); Gronostajski, R. et al., *J. Biol. Chem.*, 260:3344-3349 (1985) In cells deprived of insulin or serum, the breakdown of the average cell proteins increases up to 2-fold. This accelerated proteolysis involves the lysosomes, which are also the sites for the breakdown of endocytosed and membrane protein. Another system by which skeletal muscle can increase overall proteolysis involves the $Ca^{2+}$-dependent proteases (calpains I and II). In dystrophic or damaged muscle or in normal muscle after treatments that raise intracellular $Ca^{2+}$, overall protein breakdown rises, due mainly to activation of the calpains. In addition, there is a nonlysosomal degradative system that functions independently of ATP; in erythrocytes, this system catalyzes the selective breakdown of oxidant-damaged proteins. The relative importance of these systems in the degradation of different cell components under various conditions in muscle is unknown.

In the process requiring Ub, the first step in degradation of many proteins involves their conjugation to this small polypeptide by an ATP-requiring process. The ubiquitinated proteins are then degraded by a 1000-1500 kDa (26S) ATP-dependent proteolytic complex, the Ub-Conjugate-Degrading Enzyme ("UCDEN"). This pathway has been best characterized in reticulocytes, but has also been demonstrated in skeletal muscle and other cells. It is believed to be responsible for the rapid degradation of highly abnormal proteins and many short-lived enzymes or regulatory proteins.

A large (700 kDa) multimeric protease in eukaryotic cells, referred to as the *proteasome*, is a component of UCDEN. It contains 12-15 distinct subunits and three distinct peptidases of different specificities. By itself, the proteasome is unable to degrade ubiquitinated proteins and provides most of the proteolytic activity of UCDEN.

SUMMARY OF THE INVENTION

The present invention relates to a method of inhibiting (reducing or preventing) the accelerated breakdown of muscle proteins which accompanies various physiological and pathological states and is responsible to a large extent for the loss of muscle mass (atrophy) which follows nerve injury, fasting, fever, acidosis and certain endocrinopathies. As described herein, it has been shown that the nonlysosomal ATP-ubiquitin-dependent proteolytic process increases in muscle in these conditions and is responsible for most of the accelerated proteolysis which occurs in atrophying muscles. This is supported by the demonstration, also described herein, that there is a specific increase in ubiquitin mRNA, induction of mRNA for proteasome and increased ubiquitinated protein content in atrophying muscles which is not seen in non-muscle tissue under the same conditions.

The present invention further relates to a novel ATP-dependent protease which is involved in degradation of ubiquitinated proteins, forms a complex with the proteasome and appears to be part of the 1300-1500 kDa ATP-dependent proteolytic complex (UCDEN referred to as the 1500 kDa complex) which rapidly degrades proteins conjugated to ubiquitin. This novel protease, referred to as multipain, appears to play a critical role in the ATP-ubiquitin-dependent pathway.

Multipain is a multimeric enzyme of molecular weight approximately 500 kDa, which requires ATP hydrolysis for activation and degrades ubiquitinated proteins preferentially. This new ATP-dependent enzyme appears to be a thiol protease and has been shown to cleave Ub-conjugated proteins to acid-soluble products. Multipain has been identified in muscle and shown to play an essential role in the cytosolic pathway which is activated in various forms of muscle wasting.

The present invention further relates to purified multipain, obtained from sources in which it normally is found, such as skeletal muscle cells; DNA or RNA encoding multipain; multipain produced by recombinant DNA methods; antibodies specific for the enzyme; methods of using multipain; and multipain inhibitors and their use, particularly for reducing the loss of muscle mass which occurs in a variety of diseases or conditions.

New multipain inhibitors can be designed and produced, using knowledge of the enzyme and its structure, as described herein, and art-recognized methods. For example, knowledge of the various subunits of multipain, such as the proteolytic subunit, the ATPase and the ubiquitin-binding component, will be useful for this purpose. The present invention further relates to a method of identifying existing compounds or molecules which are inhibitors of multipain or a component of this multimeric enzyme. For example, multipain has been shown to be inhibited by cystatin A. Therefore, cells expressing cloned multipain can be used to assay cystatin analogues for their ability to inhibit the enzyme, as well as to identify other multipain inhibitors. It is also possible to screen microbial broths for antibiotic inhibitors of multipain. Multipain inhibitors can be a peptide, a peptide-like molecule, or a peptide derivative such as a peptide aldehyde, a β-lactam derivative, a peptide chloromethyl ketone, an epoxide or a peptide isocoumarin.

As also described herein, the present invention relates to a 40 kDa proteasome regulator. The 40 kDa polypeptide has been purified and shown to be a member of the large complex which binds ATP and inhibit the peptidase (degradative) activities of the proteasome.

The availability of the naturally-occurring 40 kDa inhibitor makes it possible to define the structural requirements for inhibition of the proteasome, identify the active region(s) or fragment(s) of this regulatory peptide and design novel proteasome inhibitors or identify existing compounds which inhibit the proteasome.

A multipain inhibitor or an inhibitor of another component of the 1500 kDa complex can be administered to an individual in whom loss of muscle mass occurs (e.g., following nerve injury, fasting, infection or certain endocrinopathies). Muscle mass losses in such conditions are due in turn to accelerated breakdown of muscle proteins, which has been shown, as described herein, to be due largely to activation of the non-lysosomal ATP-ubiquitin-dependent pathway, in which multipain is involved. Administration of a multipain inhibitor or an inhibitor of another component of the ATP-dependent proteolytic complex will interfere with or reduce enhanced protein breakdown which normally occurs in such conditions. As a result, proteolysis is reduced and muscle protein loss occurs to a lesser extent than normally occurs in such conditions. This method of inhibiting multipain or another component of the 1500 kDa complex and, as a result, of inhibiting destruction of muscle protein, can be used in a wide variety of conditions, such as cancer, chronic infectious diseases, fever and muscle disuse and denervation, in which it occurs and often can be extremely debilitating. The method is also useful in conditions of renal failure in which acidosis occurs or hepatic failure because it is possible to reduce the generation of amino acids and, thus, to reduce the nitrogenous load on the diseased kidneys or liver.

BRIEF DESCRIPTION OF THE DRAWINGS

FIG. 1 is a graphic representation of the results of fractionation of extracts from rabbit skeletal muscle fraction II by mono-Q anion exchange chromatography. Subsequent analysis focused on peak 2 because it was shown, as described herein, to account for most of the ATP-stimulated breakdown of lysozyme, had strong activity against oxidant-damaged hemoglobin and had little activity against the SLLVT-MCA, a characteristic substrate of the proteasome.

FIG. 2 is a graphic representation of analysis using gel filtration of the Ub-$^{125}$I-lysozyme conjugate degrading activity of peak 2, in which samples were assayed for Ub-$^{125}$I-lysozyme with (▲) or without (△) ATP and against OH/O$_2$-treated $^{14}$C-hemoglobin (●). Molecular mass markers used were blue dextran, thyroglobulin, ferritin and β-amylase.

FIG. 3 shows results of SDS-polyacrylamide gel electrophoresis (10%) of the 500 kDa protease, in which the peak of activity degrading Ub-$^{125}$I-lysozyme from the Superose 6 column was concentrated, and 25 μg protein was analyzed.

DETAILED DESCRIPTION OF THE INVENTION

Figure 1:
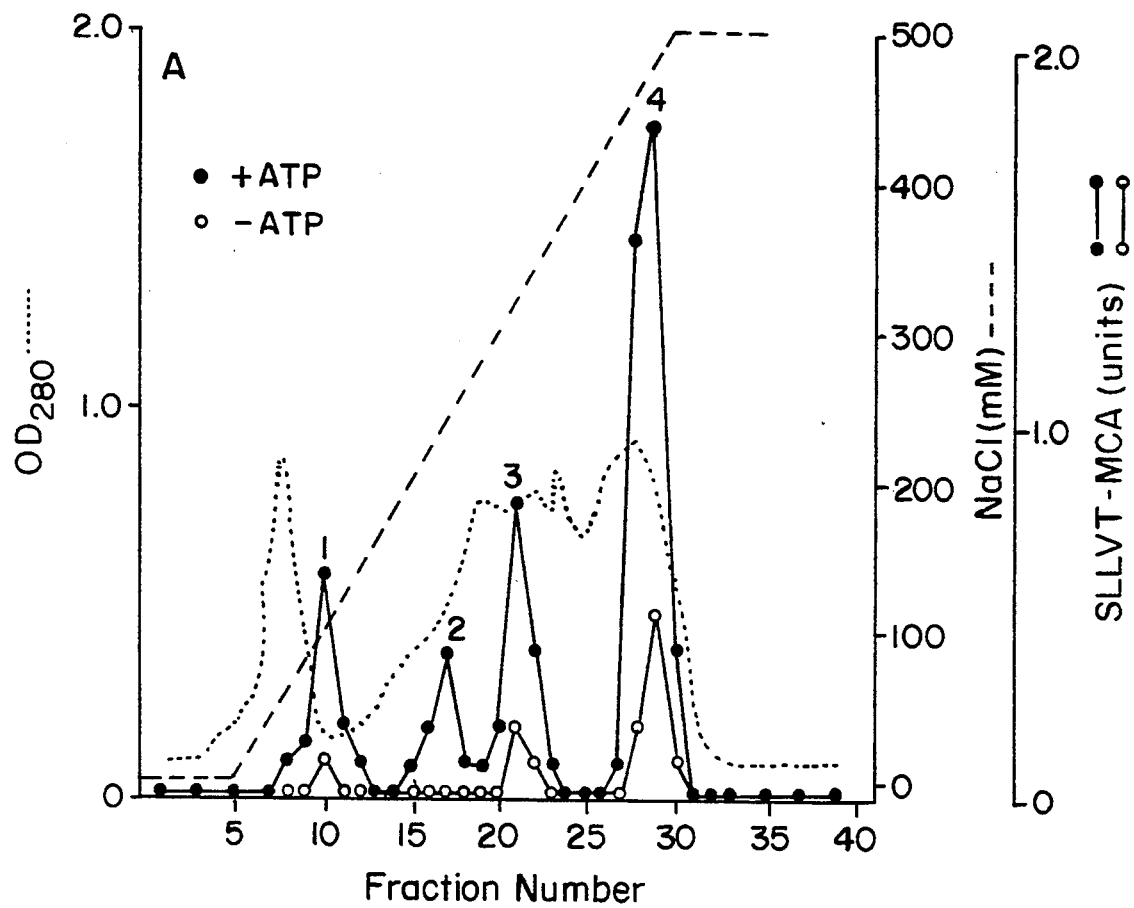
FIGS. 1–3 show steps in the purification of the 500 kDa protease.

The present invention is based on the identification of the pathway responsible for the excessive protein degradation which occurs in conditions or disease states in which there is severe loss of body mass (e.g., cachexia) and negative nitrogen balance and the discovery of constituents of this pathway, which make it possible to inhibit the pathway and the negative nitrogen balance in these catabolic states.

As described herein, work undertaken to learn which of the proteolytic systems is responsible for the large increase in protein breakdown in skeletal muscle during denervation atrophy, fasting and other catabolic states (e.g., fever) has shown that most of the accelerated proteolysis in muscle in fasting or denervation atrophy is due to activation of the nonlysosomal (cytosolic) ATP-ubiquitin-dependent proteolyte process, which until now has been generally believed to be a constitutive process (often termed "basal protein breakdown") and to be primarily responsible for the elimination of abnormal or short-lived regulatory polypeptides. As described herein, however, it has been shown that there is a specific cellular response which leads to loss of muscle protein and is triggered by a variety of physiological and pathological stimuli. For example, in fasting, the enhancement of muscle protein breakdown requires glucocorticoids and low insulin and in febrile infections, requires interleukin-1 and TNF. As is also described herein, ubiquitin is critical in enhancing the activity of the nonlysosomal ATP-dependent process in muscle in denervation atrophy, fasting, and treatment with hormones or endotoxin.

It is possible that multiple steps in the ATP-Ub-dependent pathway are affected in muscle by fasting and denervation, but the work described herein has resulted in isolation of a new, rate-limiting component in the large (1500 kDa) enzyme complex which hydrolyzes cell protein which are marked for degradation by covalent linkage to the cofactor ubiquitin. Thus, the work described herein has identified a key target for inhibition. As described, a protease has been identified in muscle and has been shown to play an essential role in the cytosolic ATP-ubiquitin-dependent proteolytic pathway now known to be activated in various forms of muscle wasting. As further described, a polypeptide inhibitor of the proteasome's degradative activities has also been identified.

The present invention relates to a method of inhibiting (reducing or preventing) the accelerated or enhanced proteolysis which occurs in atrophying muscles and is now known to be due to activation of the nonlysosomal ATP-requiring process in which ubiquitin plays a critical role. In the present method, the accelerated proteolysis is inhibited by interfering with the ATP-Ub-dependent pathway at one or more possible steps (e.g., by reducing ubiquitin conjugation of proteins, by interfering with activity of UCDEN, or by interfering with activity of one of its components, such as the novel protease multipain or the natural inhibitor).

The present invention also relates to the discovery in muscle of the protease which requires ATP hydrolysis for function and has an essential role in the cytosolic ATP-ubiquitin-dependent proteolytic pathway activated in various forms of muscle wasting. This proteolytic enzyme, called "multipain", is a 500 kDa multimer or protein complex which appears to be a thiol protease related to the papain family of proteases. It contains 6 or more high molecular weight subunits (50-130 kDa in size) and has been shown to degrade ubiquitin-conjugated proteins preferentially, by an ATP-dependent reaction. A variety of observations, also described herein, indicate that this protease is the rate limiting component in the recognition and degradation of proteins conjugated to ubiquitin. Multipain also has the ability to depolymerize the multiple-ubiquitin chain by an isopeptidase activity. It is sensitive to sulfhydryl blocking agents, cystatin and related polypeptides and peptide chloromethylketones, but not to leupeptin, E-64 or serine protease inhibitors. In the presence of ATP, multipain forms a 1:1 complex with the proteasome; complex formation is blocked by cystatin.

Thus, inhibition of the ATP-ubiquitin-dependent pathway is a new approach for treating the negative nitrogen balance in catabolic states. This can be effected, for example, through use of an inhibitor of the newly discovered proteolytic enzyme, resulting in reduction of loss of muscle mass in conditions in which it occurs. Such an inhibitor can also be used in reducing the activity of the cytosolic ATP-ubiquitin-dependent proteolytic system in cell types other than muscle cells. Excessive protein loss is common in many types of patients, including individuals with sepsis, burns, trauma, many cancers, chronic or systemic infections, neuromotor degenerative disease, such as muscular dystrophy, acidosis or spinal or nerve injuries. It also occurs in individuals receiving corticosteriods, and those in whom food intake is reduced and/or absorption is compromised. Moreover, inhibitors of the protein breakdown pathway could possibly be valuable in animals (e.g., for combating "shipping fever", which often leads to a major weight loss in cattle or pigs).

The following is a description of the work which led to the discovery that most of the accelerated proteolysis in muscle in these conditions is due to activation of the nonlysosomal ATP-requiring process; isolation and characterization of the protease multipain; its function in proteolysis; isolation and characterization of a 250 kDa naturally-occurring inhibitor of the proteasome; a method of identifying multipain inhibitors and inhibitors identified by these methods and a method of inhibiting multipain and its effect on muscle degradation.

Demonstration That the Cytosolic ATP-Dependent Proteolytic Pathway Is Critical in Atrophy of Skeletal Muscle As described herein, particularly in Examples 3–5, assessment of whether the accelerated proteolysis evident in atrophy of skeletal muscles upon denervation or fasting is catalyzed by the nonlysosomal ATP-dependent or energy-independent degradative systems has been carried out. This work has clearly demonstrated a link between the nonlysosomal ATP-dependent pathway and muscle wasting. As described herein, it has been shown that in a variety of catabolic states (e.g., denervation, fasting, fever, certain endocrinopathies or metabolic acidosis) muscle wasting is due primarily to accelerated protein breakdown and, in addition, that the increased proteolysis results from activation of the cytosolic ATP-ubiquitin-dependent proteolytic system, which previously had been believed to serve only in the rapid elimination of abnormal proteins and certain short-lived enzymes. The discovery that this pathway is responsible for the accelerated proteolysis in these catabolic states is based on studies in which different proteolytic pathways were blocked or measured selectively in incubated muscles, and the finding of increased mRNA for components of this pathway (e.g. for ubiquitin and proteasome subunits) and increased levels of ubiquitin-protein conjugates in the atrophying muscles. As described herein, simple animal models that closely mimic these catabolic states (e.g., disuse, atrophy, sepsis, endotoxin-treatment, which mimics fever and muscular dystrophy) have been developed, as have methods for precise measurement of rates of protein breakdown in muscles during in vitro incubations.

Results showed that when normal skeletal muscles incubated in vitro were depleted almost completely of ATP, protein breakdown decreased by 40–70%. The ATP-dependent (nonlysosomal) proteolytic process was found to be measured specifically and reproducibly if the residual ATP-dependent process was subtracted from the total protein breakdown seen in the control contralateral muscle. Within 1 and 3 days after denervation of the soleus, this ATP-dependent process increased by 50–250%, while the residual (energy-independent) process did not change. The rise in this ATP-dependent, nonlysosomal process accounted for all of the increased protein breakdown during denervation atrophy, including the rapid degradation of actin (as shown by increased 3-methylhistidine production). This response again accounted for most of the enhanced protein breakdown in fasting.

After food deprivation, ATP-dependent proteolysis in the muscles increased selectively by 150–350%. After refeeding, this process returned to control levels within 1 day. In addition, in muscle extracts from fasted rabbits, the ATP-dependent degradation of endogenous proteins and $^{14}$C-casein was about 2-fold faster than in extracts from fed animals. Similarly, selective increase in ATP-dependent proteolysis in muscles occurred in sepsis, as modeled by the injection of endotoxin (LPS).

Thus, as shown herein, the increase in the ATP-dependent process in muscle is a specific cellular response, activated in a variety of catabolic states, which appears responsible for most of the accelerated proteolysis in atrophying muscles. The conditions which influence the ATP-requiring degradative system include denervation atrophy, fasting, fever, certain endocrinopathies and acidosis.

Activation of the ATP-Ubiquitin-Dependent System in Muscle During Fasting and Denervation Atrophy As described above, activation of an ATP-dependent proteolytic process appears responsible for most of the increased protein degradation in skeletal muscle during fasting and denervation atrophy. Because this process might involve the activation of the ATP-ubiquitin-dependent pathway, the levels of mRNA for ubiquitin (Ub) and Ub protein content in such atrophying muscles were measured (See Example 6). After food deprivation of rats for 1 day, a 2- to 4-fold increase in the levels of two polyUbiquitin transcripts (2.4 and 1.3 kDa) was detected in the soleus and extensor digitorium longus muscles, although their total RNA and total mRNA content fell by 50%. After denervation of the soleus, a 2- to 3-fold increase in polyUb mRNA also occurred within 1 day, while total RNA content fell. The increase in Ub mRNA upon fasting or denervation was accompanied by a 60–90% rise in the total content of ubiquitin in these muscles. When fasted animals were refed, the levels of Ub mRNA in their muscles returned to control levels within 1 day.

Isolation and Characterization of the Protease Multipain

As discussed above, degradation of many proteins in eukaryotic cells involves their conjugation to a small polypeptide, ubiquitin, by an ATP-requiring process. UCDEN (Ub-Conjugate Degrading Enzyme or megapain) degrades the ubiquitinated proteins. The precise nature of UCDEN is unclear, although it has been shown that the 1000–1500 kDa (26S) complex can be formed in extracts of energy-depleted reticulocytes by an ATP-dependent association of three components, referred to as CF-1, CF-2 and CF-3 (Ganoth, D. et al., *J. Biol. Chem.* 263:12412–12419 (1988)). Proteasome, also discussed above, has been shown to be one of the components (CF-3) of UCDEN (Eytan, E. et al., *Proc. Natl. Acad. Sci. USA*, 86:775107755 (1989); Driscoll, J. and A. L. Goldberg, *J. Biol. Chem.* 265:4789–4792 (1990)). However, until now, the nature and function of the two other components were unknown.

Summary of the Characteristics of Multipain

As described below, a new type of protease has been identified in skeletal muscle and shown to be part of the UCDEN complex. The new protease, multipain, forms a complex of approximately 1500 kDa with the proteasome and appears to correspond to an active form of the CF-1 component of UCDEN. Unlike the proteasome, multipain:

a) by itself degrades ubiquitinated proteins in an ATP-dependent process and has little or no activity against typical proteasome substrates, such as N-succinly-Leu-Leu-Val-Tyr-7-amino-4-methylcoumarin (sLLVT-MCA) and casein;

b) is sensitive to cystatin A (an inhibitor of papain-like enzymes) and to certain low-molecular weight inhibitors (e.g., hemin or certain peptide chloromethylketones), but is not sensitive to inhibitors of serine proteases (e.g., diisopropylfluorophosphate) and, thus, appears to be a thiol protease;

c) does not react with anti-proteasome antibodies; and d) includes a set of at least 6 major subunits (50–150 kDa) and none of the characteristic 20–30 kDa subunits of the proteasome.

The new protease has also been shown to degrade nonubiquitinated protein (e.g., lysozyme) by an ATP-dependent process, although at a slower rate than it degrades ubiquitinated protein (ubiquitinated lysozyme), and to degrade oxidant-damaged hemoglobin by an ATP-independent mechanism. The new protease has been shown to play a critical role in the key cytosolic (nonlysosomal) protein degradative pathway and to function synergistically with the proteasome (as a constituent of a complex comparable in size to UCDEN) in the ATP-dependent degradation of ubiquitinated proteins. In the large complex, multipain appears to catalyze initial cleavages of ubiquitin-conjugated proteins. Taken together, the findings presented herein indicate that multipain is the rate-limiting component in the recognition and degradation of ubiquitin-conjugated proteins.

Purification of Multipain

As described in detail in Example 1, the new protease has been obtained from mammalian skeletal muscle. Briefly, muscles were obtained and processed, as described in Example 1, in order to isolate the fraction which included the activity degrading Ub-protein conjugates. The activity-containing fraction was further separated by chromatography into two peaks with Ub-protein (Ub-$^{125}$I-lysozyme)-degrading activity. Peak 2 was shown to account for most of the ATP-stimulated breakdown of ubiquitinated lysozyme and to have strong activity against oxidant-damaged hemoglobin, but little activity against N-succinyl-Leu-Leu-Val-Tyr-7-amino-4-methylcoumarin (sLLVT-MCA), which is a characteristic substrate of the proteasome (FIG. 1). The activity was further purified and a single active peak of molecular mass approximately 440,000 was obtained. It has an apparent molecular weight of 540 kDa.

Characterization of Multipain

Characterization of the purified protease showed that it is a set of at least 6 major subunit bands (Mr values 40,000–150,000) and does not contain any of the 20–30 kDa bands characteristic of the proteasome.

The catalytic properties of the protease were assessed (Example 1). Hydrolysis of Ub-lysozyme was stimulated 5-fold by the addition of ATP and the degradation of lysozyme was stimulated 3-fold. In contrast, degradation of native and of oxidant-damaged hemoglobin by the protease was independent of ATP. The oxidant-damaged hemoglobin was degraded 15 times faster than the native hemoglobin.

The protease was also shown to have a clear preference for the ubiquitinated substrate (as opposed to the non-ubiquitinated substrate). The proteasome, in contrast, showed little, if any, activity against the Ub-conjugate. The nature of the proteolytic reaction by which the protease degraded Ub-conjugates was assessed by determining the size of the acid-soluble products generated from Ub-$^{125}$I-lysozyme. This assessment showed that the protease is an endopeptidase and appears to lack exopeptidase activity.

The possibility that the new protease shared common components with the proteasome was investigated using a monoclonal antibody against the human liver particle (Table II; Matthews, W. et al., Proc. Natl. Acad. Sci. USA, 86:2597–2601 (1989)) and a polyclonal antibody against the rat liver proteasome (Example 1). These treatments demonstrated no cross-reactivity between the new protease and the proteasome. This lack of cross-reactivity was confirmed by Western blot analysis; the two antibodies failed to react with the new protease.

Effects of Enzyme Inhibitors on Multipain

The effects of various types of enzyme inhibitors on the new protease were also assessed, as described in Example 1. Results are presented in Table I. Diisopropylfluorophosphate (DFP), an irreversible inhibitor of serine proteinases, did not affect conjugate breakdown. o-Phenanthroline, which chelates heavy metals, showed some inhibition. In contrast, N-ethylmaleimide (NEM), a thiol-blocking reagent, and egg-white cystatin (cystatin A), a potent inhibitor of many papain-like thiol proteases, strongly inhibited this activity. At similar concentrations, cystatin B (stefin B) showed 55% inhibition and no significant effect was detected with cystatin C. Although this new activity thus appears to be a thiol protease, it was only inhibited by 30% in the presence of leupeptin and not at all by E64, both inhibitors of many thiol proteinases (e.g., lysosomal enzymes or calpains). However, the susceptibility to leupeptin and E64 is strongly influenced by the sequences preceding the sessile bond and not all thiol proteases are sensitive to them. Hemin, which can inhibit completely the ATP-Ub-dependent proteolytic system and the proteasome, also blocked conjugate-degrading activity by the new protease.

These results suggest that the new enzyme has a thiol residue in its active site. The pattern of effective inhibitors clearly differentiates the activity of this new enzyme from the proteasome, which when activated acts as a serine protease with multiple catalytic sites. The effects of the different inhibitors on degradation by the new protease of $^{125}$I-lysozyme (non-Ub) and oxidant-damaged hemoglobin showed similar results as with Ub-lysozyme. This suggests that a single type of active site is involved in the hydrolysis of these different types of proteins.

Assessment of whether ubiquitinated and nonubiquitinated proteins are bound to the same site on the new protease was carried out (Example 1). Results failed to demonstrate competition among lysozyme, hemoglobin and oxidant-treated hemoglobin (i.e., none of these substrates reduced the degradation of Ub-$^{125}$I-lysozyme). This suggests that the new protease has specific binding domains which recognize both ubiquitinated and nonubiquitinated protein substrates.

The Multipain-Proteasome Complex

The new protease was shown to form a 1500 kDa complex with extensively purified proteasome when the two were incubated in the presence of ATP and $Mg^{2+}$. The resulting complex was shown to degrade ubiquitinated lysozyme and the Ub-conjugate-degrading activity could be blocked by immunoprecipitation with anti-proteasome antibodies.

Figure 6:
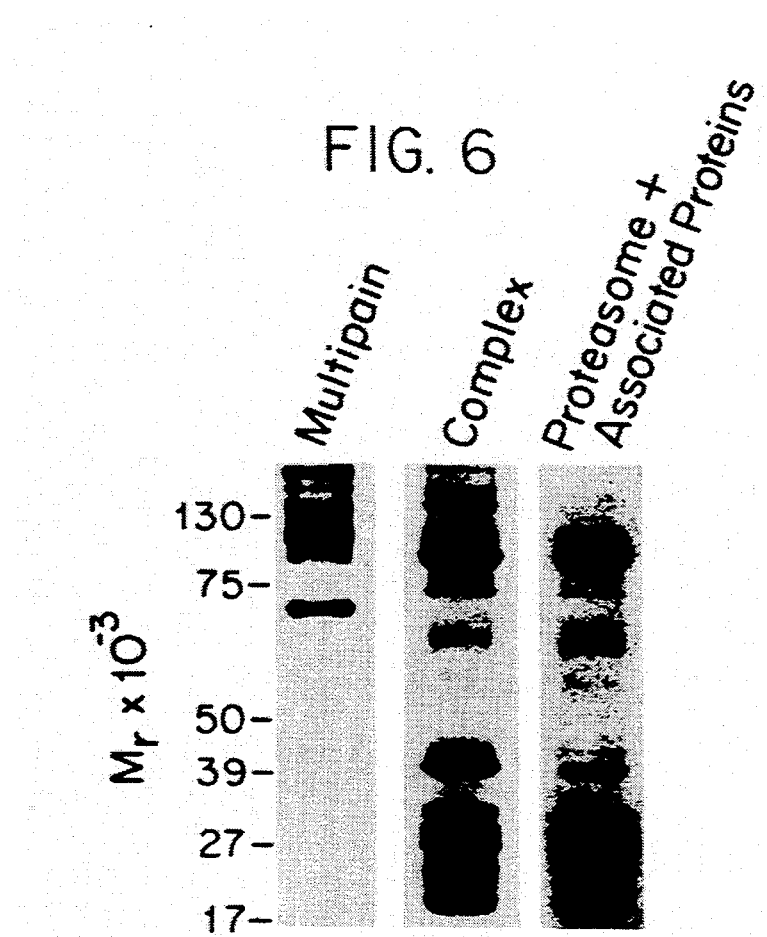
FIG. 6 shows results of SDS-polyacrylamide gel electrophoresis of multipain, the proteasome-multipain complex and partially purified proteasome.

The complex formed between multipain and proteasome in vitro appears very similar or identical to the 1500 kDa Ub-conjugate degrading enzyme, or 26 s proteolytic complex UCDEN, isolated previously from reticulocytes and muscle. These structures are of similar sizes, are labile, and are activated by the same nucleotides. They degrade the same substrates (Ub-lysozyme conjugates, casein, and fluorometric peptides) and are sensitive to the same groups of inhibitors. The complexes described here, like those isolated previously, contain the characteristic 20–30 kDa proteasome subunits, plus a number of larger subunits, including the six large polypeptides found in multipain. The complex formed here contains at least 10–12 polypeptides of 40–150 kDa (FIG. 6).

A variety of observations (Example 2) suggest that the proteasome and multipain are present in equal amounts in the complex. The findings described herein also show that the proteasome and multipain function synergistically in the ATP-dependent degradation of ubiquitinated proteins. For example, as described in Example 2, when multipain alone degraded Ub-$^{125}$I-lysozyme, the only $^{125}$I product was a peptide of about 11 residues. However, the proteasome-multipain complex degraded this substrate more rapidly (Example 2) and generated only smaller $^{125}$I-peptides of about 3 and 5 residues.

Isolation of a An Endogenous Inhibitor of the Proteasome

As described in Example 7, a 40 kDa polypeptide regulator of the proteasome, which inhibits the proteasome's proteolytic activities has been purified from reticulocytes and shown to be an ATP-binding protein whose release appears to activate proteolysis. The isolated inhibitor exists as a 250 kDa multimer and is quite labile (at 42° C.). It can be stabilized by the addition of ATP or a nonhydrolyzable ATP analog, although the purified inhibitor does not require ATP to inhibit proteasome function and lacks ATPase activity. The inhibitor has been shown to correspond to an essential component of the 1500 kDa proteolytic complex. If reticulocytes are depleted of ATP, the 1500 kDa UCDEN is not found. Instead, Ganoth et al. identified three components, designated CF-1, CF-2 and CF-3, referred to above. The inhibitor isolated as described herein appears identical to CF-2 by many criteria. These findings indicate the idea that the inhibitor plays a role in the ATP-dependent mechanism of the UCDEN complex. It is possible, for example, that during protein breakdown, within the 1500 kDa complex ATP hydrolysis leads to functional release of the 40 kDa inhibitor, temporarily allowing proteasome activity, and that ubiquitinated proteins trigger this mechanism.

The purified factor has been shown to inhibit hydrolysis by the proteasome of both a fluorogenic tetrapeptide and protein substrates, as described in Example 7. When the inhibitor, the proteasome and partially purified CF-1 were mixed in the presence of ATP and $Mg^{2+}$, the 1500 kDa complex was reconstituted and degradation of Ub-$^{125}$I-lysozyme occurred.

Isolation of this inhibitor of the multiple peptidase activities of the proteasome makes available an attractive site for pharmacological intervention. As described subsequently, this provides a natural inhibitor whose structural and functional features can be assessed to provide information useful in developing proteasome inhibitors.

Uses of the Present Invention

The present findings should alter currently widespread views about the physiological roles of the soluble ATP-Ub-dependent pathway, which is generally believed to be a constitutive process (often termed "basal protein breakdown") and to be primarily responsible for the elimination of abnormal or short-lived regulatory polypeptides. As shown herein for the first time, the loss of body mass and negative nitrogen balance characteristically seen in many disease states or conditions is the result of accelerated or excessive protein degradation carried out via this pathway. The muscle wasting which occurs upon denervation, fasting, fever or metabolic acidosis is due mainly to this accelerated protein breakdown. Now that the responsible pathway and key constituents (e.g., multipain and a natural proteasome regulator) have been identified, it is possible to reduce or abolish the accelerated protein breakdown and, thus, the loss of body mass and the negative nitrogen balance. Multiple steps in the ATP-Ub-dependent pathway may be affected in muscle by fasting and denervation, but one clear point of regulation is the rate of production of Ub mRNA, as shown in Example 6. In addition, increased conjugation of muscle proteins to ubiquitin has been shown under these conditions.

Such findings can serve as the basis for effective methods for reducing this proteolytic process and, thus, combatting negative nitrogen balance and muscle wasting in such conditions as cachexia associated with diseases including various types of cancer and AIDS, febrile infection, denervation atrophy (inactivation and disuse), steroid therapy and surgery. This can be useful in reversing or avoiding a feature of such diseases or conditions which can be severely debilitating and seriously compromise an individual's ability to recover. In particular, partial inhibition of the ATP-ubiquitin-dependent pathway is an approach to treatment. This results in reduction (total or partial) of the accelerated protein breakdown which occurs in numerous physiological and pathological states, but does not affect normal degradative processes carried out via this process.

As a result of the work described herein, multipain is available and has been shown to play a critical role in the cytosolic proteolytic pathway which has been shown to be activated in various forms of muscle wasting. The availability of purified multipain of the present invention makes it possible to define the enzyme's active site or proteolytic subunit, using known methods. For example, since proteolysis is inhibited by cystatin (Ki<1 uM), affinity chromatography of the active subunit can be done using chicken cystatin as the ligand, as has been done with papain. Alternatively, crosslinking of $^{125}$I-labelled cystatin to multipain using bifunctional reagents, such as diethylsuberimidate, should also make it possible to label the cystatin-binding component. Alternatively, radioactive peptide chloromethylketones (CKs) can be used to covalently label the active sites. In addition, new approaches for chemically tagging these inhibitors with $^{125}$I have been developed. By removing the blocking CBZ residue from CBZ-Ala-Arg-Arg-MNA, and reacting it with $^{125}$I-Bolton-Hunter reagent, we have found it possible to label this inhibitor to high specific activity. The active site of multipain can be labelled. Once such active subunits are identified, the critical polypeptide can be cloned, as described below.

The functions of other multipain subunits can also be defined. For example, it is of interest to define the function of the ATP-binding subunit, (which presumably is an ATPase) and to identify the subunit responsible for the isopeptidase activity, which depolymerizes polyubiquitin chains and regenerates free ubiquitin. Once the active site or subunit has been identified, it can be crystallized, and the characteristics (coordinates) of the crystal structure used as the basis for rational drug design. For example, the active subunit can be crystallized in complex with a known inhibitor, such as cystatin A, and the resulting information about the interaction used to design multipain inhibitors, which can be "cystatin-like" substances (substances which are cystatin analogues) or other molecules which bind the multipain active site and prevent multipain from acting, individually or as a member of the complex it forms. Inhibitors can be, for example, peptides or peptide-like molecules (e.g., a peptide aldehyde, a peptide chloromethyl ketone or a peptide isocoumarin). Knowledge of the multipain active site structure will make it possible to design drugs which can be used to interfere with the ATP-dependent proteolytic process in which multipain is a key participant and whose activation, as shown for the first time herein, is responsible for most of the increased protein degradation which occurs in skeletal muscle during fasting, denervation and infection. Inhibitors can be produced which interact specifically with a particular subunit or polypeptide which is a component of multipain.

Purified multipain can also be used to obtain peptide sequence information for preparation of oligonucleotide probes, which can, in turn, be used to clone multipain from human and other mammalian cDNA libraries. The amino acid sequence of a portion of the purified multipain can be obtained, using known methods (e.g., Sambrook, J. et al., *Molecular Cloning; a Laboratory Manual*, 2d edition, Cold Spring Harbor Laboratory Press, 1989), and the nucleotide sequence encoding the amino acid sequence deduced. Oligonucleotides having the deduced sequence can be prepared, using known methods (e.g., Sambrook, J. et al., *Molecular Cloning; a Laboratory Manual*, 2d edition, Cold Spring Harbor Laboratory Press, 1989)), and used to probe human or other mammalian cDNA libraries for sequences which hybridize to the probe. The cDNA sequences obtained from the libraries can then be incorporated into an appropriate vector (e.g., pBR322, pUC) and expressed in an appropriate host (e.g., *E. coli*, K12), resulting in recombinantly-produced multipain or multipain components. The identity of the multipain produced in this manner can be verified using known techniques (e.g., those based on physical characteristics, reactivity with an antibody known to react with purified multipain and assessment of its ability to complex with the proteasome).

Expression of the cloned gene in *E. coli* is useful to increase availability of the proteolytic subunit of multipain. Although it is desirable to obtain the proteolytic subunit in an active form, other subunits of multipain may be necessary for its proper folding and stability. The availability of large amounts of this subunit will make it possible to crystallize it, either by itself or in complexes with cystatin. The resulting crystals can be subjected to X-ray diffraction analysis and information about the crystal structure can be used in designing new drugs or selecting existing drugs which can inhibit multipain.

The multipain gene can be sequenced and oligonucleotide probes based on that nucleotide sequence (probes which identify or hybridize to the multipain gene) can be used to identify similar genes in other mammals, as well as in other types of cells. As used herein, the term multipain genes is intended to include DNA encoding the purified multipain obtained as described, DNA encoding a multipain subunit, DNA encoding a protein or polypeptide which has substantially the same activity and functional characteristics as those of the purified multipain obtained as described herein and DNA which hybridizes to the oligonucleotide probes based on the multipain genes.

Antibodies which are reactive with or recognize multipain can be produced using known methods and are also the subject of the present invention. Polyclonal sera can be produced by injecting an appropriate animal host (e.g., rabbit, mouse, monkey) one or more times with purified or recombinantly-produced multipain and obtaining blood from the animal after an appropriate time for antibody production to have occurred. Monoclonal antibodies can be produced using known techniques, such as that of Kohler and Milstein. Antibodies produced in either manner can be used to identify multipain or subunits in other tissues and other animals.

As described herein, Ub mRNA levels increase (i.e., the polyUb gene is specifically induced) under conditions where there is enhanced ATP-dependent protein degradation (e.g., atrophying muscle, fasting). These levels return to normal when the enhanced degradation is reversed (e.g., by refeeding). An appropriate oligonucleotide probe can be constructed to detect the Ub mRNA and determine whether it is present in greater than normal quantities. This can be used as an indicator of accelerated protein degradation.

Cells in which the multipain gene is expressed (e.g., cell lines in which it is expressed) can be used to screen inhibitors. Alternatively, the purified multipain or the recombinantly-produced multipain can be used to screen for inhibitors. Screening potential multipain inhibitors can be carried out by determining the ability of a potential inhibitor to interfere with activity of the protease. For example, a potential inhibitor can be combined with multipain, a ubiquitinated protein substrate (e.g., ubiquitinated lysozyme), ATP and $Mg^{2+}$, under condition appropriate for the protease to degrade the ubiquitin-protein conjugate. A control which includes the same components except for the potential inhibitor is used for comparative purposes. Inhibitors are identified by their ability to reduce degradation of the conjugate. Microbiol broths can similarly be screened for antibiotic inhibitors of multipain.

Multipain inhibitors, as well as proteasome inhibitors and UCDEN inhibitors, can be used to reduce (totally or partially) the nonlysosomal ATP-dependent protein degradation shown to be responsible for most of the increased protein degradation which occurs during fasting, denervation or disuse (inactivity), steroid therapy, febrile infection and other conditions. As described herein, cystatin is a multipain inhibitor and can be used to interfere with multipain function, individually or as part of the 1500 kDa complex it forms with the 700 kDa proteasome. Cystatin analogues or other molecules which interfere with multipain and/or complex formation can also be used.

It is possible to assess low molecular weight protease inhibitors for their ability to inhibit multipain or to be modified in such a manner that they inhibit multipain. For example, E-64 and its derivatives are potent inhibitors of most thiol proteases. They are, however, unable to inhibit multipain. Many new analogs and derivatives of E-64 have been synthesized and these, as well as additional derivatives designed based on the present work, can be assessed for their ability to inhibit multipain. Various peptide chloromethyl ketones (CKs) react irreversibly with active site histidines in both serine and thiol proteases. Certain tripeptide CKs (e.g. CBZ-ala-arg-arg-CK) have been shown to inactivate multipain and the 1500 kDa complex at relatively low concentrations (50 uM). Such agents can be made very specific by tailoring the peptide sequence and thus multipain-inhibiting ability assessed. Other compounds which can be assessed include peptide diazomethanes, which are selective inhibitors of thiol proteases, isocoumarins, which are heterocyclic inhibitors, and various synthetic $\beta$-lactams. Preliminary data suggests some of these compounds can inhibit the 1500 kDa ATP-dependent complex.

Of particular interest as potential multipain inhibitors are cystatin and other members of the cystatin superfamily (Stefin A and B, cystatin c, kininogen). Information about their tertiary structures in complex with papain and site-directed mutagenesis of cloned human cystatin A should be a valuable basis for defining properties, mechanisms and even the structure of multipain's proteolytis subunit.

It will be necessary to determine whether any inhibitors found to be effective against the 1500 kDa proteolytic complex can selectively inhibit protein breakdown in intact cells. This can be done as follows: First, crude extracts of muscle will be used to test the inhibitor's ability to block the entire ATP-ubiquitin-dependent pathway. Such studies can use model radioactive substrates as well as endogenous cell proteins, whose degradation can be easily followed by measuring the appearance of free tyrosine. I. C. Kettelhut, et al., *Diabetes/Metab.*, Rev. 4:751–772 (1988); M. Tischler, et al., *J. Biol. Chem.* 257:1613–1621 (1982). Promising agents are then tested on intact rat muscles and cultured cells, in order to evaluate their efficacy against the intracellular proteolysis, their ability to permeate mammalian cells, and their effects on cell viability.

A particularly useful approach to testing drug candidates for their ability to inhibit the ATP-ubiquitin-dependent degradative process is to do so in cultured cells in which a short-lived protein whose degradation is ubiquitin-dependent is produced. Inhibition of the process leads to accumulation of the protein in the cytosol. The extent to which the protein accumulates in the cytosol can be determined, using known methods. For example, a potential inhibitor of the process can be introduced into cultured cells producing a short-lived enzyme and the extent to which the enzyme is present in the cytosol in the presence of the potential inhibitor compared with the extent to which it occurs in its absence. Accumulation of the enzyme in the presence of the potential inhibitor is indicative of inhibition of the ATP-ubiquitin-dependent process by the potential inhibitor being tested. Cultured cells, such as COS cells, which are stably transformed with a gene encoding a short-lived protein whose degradation is ubiquitin-dependent (e.g., a short-lived enzyme, such as a mutant $\beta$-galactosidase with an abnormal amino terminus which marks it for rapid ubiquitin-dependent degradation) can be used for this purpose. For example, COS cells stably transformed with a gene encoding a mutant or recombinant form of $\beta$-galactosidase from *E. coli*, whose half-life is about 15 minutes and whose degradation is ubiquitin-dependent, can be used (Bachmair, A. et al., *Science* 234:179–186 (1986); Gonda, D. K. et al., *J. Biol. Chem.*, 264:16700–16712 (1989)). Other mutant forms of enzymes which are rapidly degraded can also be used. Accumulation of the mutant $\beta$-galactosidase in COS cytosol in the presence of a substance being assessed for its ability to inhibit the process (a potential inhibitor) is indicative of inhibition of the process. An appropriate control is COS cells maintained under the same conditions but in absence of the potential inhibitor. This approach can be used to screen for effective inhibitors from microbial broths or chemical libraries.

If a substance which blocks protein synthesis is added to such cells, the enzymatic activity and antigen (protein) disappear equally rapidly, making it possible to confirm the potential inhibitor's actions on proteolysis. Measurement of cell growth, ATP content and protein synthesis in such cells makes it possible to identify (and avoid) highly toxic substances, which is useful because any agent that depletes the cells of ATP could appear to be a potent inhibitor of proteolysis.

In inhibitor-treated cells, it would also be informative to use pulse-chase isotopic methods to follow the rates of breakdown of endogenous short-lived and long-lived proteins, especially long-lived proteins, especially ones known to be degraded by the ubiquitin dependent pathway (e.g., the oncogene products myc or fos).

Any effective inhibitors are then tested in vitro in incubated rats. In such experiments, the soleus or extensor digitorum longus muscles from one leg can be incubated with an inhibitor, while the contralateral, identical muscle serves as a control. The great advantage of such approaches is that they are highly sensitive, inexpensive, and do not require isotopic labeling of animals. I. C. Kettelhut, et al., *Diabetes/Metab.*, Rev 4:751–772 (1988); K. Furuno, et al., *J. Biol. Chem.*, 265:8550–8557 (1990). With experience, it is easy with six animals to demonstrate statistically significant changes in overall protein breakdown or synthesis as small as 10–15%. It can be calculated from the average turnover time of muscle proteins that even changes of this magnitude in proteolysis could be of therapeutic benefit; if maintained for 2 weeks, a 15% reduction in proteolysis by itself should lead to at least a doubling of mass of a denervated muscle. Also of interest will be to follow the effects of the inhibitor on breakdown of myofibrillar proteins, which constitutes 60% of the muscle mass, and represent the major protein reserve in the organism. These proteins are lost differentially upon denervation or fasting. K. Furuno, et al., *J. Biol. Chem.*, 265:8550–8557 (1990). The degradation of myofibrillar components can be followed specifically by measuring 3-methylhistidine release from muscle proteins, which is a specific assay for breakdown of actin. K. Furuno, et al., *J. Biol. Chem.*, 265:8550–8557 (1990); B. B. Lowell, et al., *Biochem. J.*, 234 (1986). It will be of particular importance to carry out such studies with muscles undergoing denervation (disuse) atrophy or ones from fasted or endotoxin-treated (febrile) animals. In such tissues, overall protein breakdown is enhanced, and thus they closely mimic the human disease, but can be studied under well-defined in vitro conditions. A demonstration of efficacy in such preparations could greatly accelerate the process of drug development.

Inhibition of the protein degradative process will be useful in a wide variety of conditions in which muscle wasting occurs and exacerbates the effects of the underlying condition, further weakening the affected individual. Such conditions include cancer, AIDS, muscle wasting after surgery or injury (due to immobilization of the individual or a limb), infection, cachexia due to any cause, corticosteroid treatment and any event or condition which activates or results in a negative nitrogen balance.

Multipain inhibitors can also be administered to counter weight loss which occurs in animals or to act as growth promoters. Since they act to inhibit protein breakdown they should promote net protein accumulation and make protein synthesis more efficient in growth promotion. For example, they can be administered to animals in order to avoid the epidemic loss of muscle mass (net protein degradation), referred to as shipping fever, that generally occurs when sheep or cattle are immobilized or confined, such as during shipping.

Multipain inhibitors of the present invention can be administered by a variety of routes (e.g., intravenously, subcutaneously, intramuscularly) and will generally be administered in combination with a physiologically acceptable carrier (e.g., physiological saline). The quantity of multipain inhibitor given will be determined empirically and will be based on such considerations as the particular inhibitor used, the condition of the individual, and the size and weight of the individual. They can be administered alone or in combination with another multipain inhibitor or an inhibitor of another pathway (e.g., a lysosomal or $Ca^{2+}$-dependent pathway) responsible for loss of muscle mass.

The present invention will now be illustrated by the following examples, which are not intended to be limiting in any way.

EXAMPLE 1

Isolation and Characterization of Multipain

Experimental Procedures

Materials

DEAE-cellulose (DE52) was purchased from Whatman Biosystems Ltd. (Maidstone, Kent, England). Ub, casein ammonium sulfate (grade I), nucleotides and N-succinyl-Leu-Leu-Val-Tyr-7-amido-4-methylcoumarin (sLLVT-MCA) were from Boehringer (Mannheim, F.R.G.). Other peptides described were from Bachem Bioscience (Philadelphia, Pa.) or from Enzyme Systems Products (Livermore, Calif.). Freshly purified human hemoglobin (1 mM) was prepared, Fagan, J. M. et al., *J. Biol. Chem.*, 261:5705–5713 (1986), and labelled with $^{14}C$-formaldehyde as described by Rice and Means. Rice, R. H. and Means, G. E. *J. Biol. Chem.* 246:831–832, (1972). To generate oxidant-damaged hemoglobin, the $^{14}$C-methylhemoglobin was exposed to .OH and .O$_2$ radicals generated by $^{60}$Co irradiation at a concentration of 50 nmol of oxygen radicals per nmol of protein. Davies, K. J. A. *J. Biol. Chem.*, 262:9895–9901 (1987). Casein and lysozyme were radiolabelled with $^{14}$C-formaldehyde and $^{125}$I, respectively, as previously described. Waxman et al., *J. Biol. Chem.*, 262:2451–2457 (1987).

Preparation of Extracts and the New Enzyme

New Zealand white rabbits (4–5 kg) were killed by asphyxiation with CO$_2$, and the psoas muscles were rapidly excised. The muscles were trimmed of fat and connective tissue, and then ground on a prechilled meat grinder. Approximately 250 g of muscle (wet weight) were suspended in ice-cold buffer (3 ml/per g of tissue) containing 20 mM TRIS-HCl (pH 8.0), 1 mM MgCl$_2$, 0.1 mM EDTA and 1 mM DTT, and then homogenized in a 1-liter Waring blender for 1 min at the top speed. All subsequent steps were carried out at 4° C. After the pH was adjusted to 7.0 using NaOH, the crude extracts were prepared by centrifugation at 10,000× g for 30 min and then ultracentrifugation of the supernatants at 100,000× g for 60 min.

After ultracentrifugation, extracts were applied to a 100-ml DE-52 column equilibrated in 20 mM TRIS-HCl (pH 7.0) and 1 mM DDT (buffer A). The column was washed until no protein was detected in the eluate, and the bound protein (Fraction II), which contains most of the ATP-dependent proteolytic activity, was eluted with buffer A containing 0.5M NaCl. The eluted proteins (Fraction II) were submitted to ammonium sulfate fractionation.

In order to remove the free proteasome from other activities, muscle fraction II was brought to 38% saturation and stirred for 45 min. The insoluble proteins were isolated by centrifugation at 10,000× g for 20 min, and the 0–38% pellet was then suspended in 20 mM TRIS-HCl (pH 7.0), 1 mM DDT. After extensive dialysis against the same buffer, this fraction was concentrated and applied to a Pharmacia Mono Q column (FPLC) equilibrated with 20 mM TRIS-HCl (pH 7.8). The fractions that degraded Ub-$^{125}$I-lysozyme (peaks 1 and 2, see FIG. 1A) were pooled, concentrated and applied to a Pharmacia Superose 6 gel filtration column equilibrated with the same buffer used for Mono Q fractionation, but containing 150 mM NaCl. A single preparation of the new enzyme involved three successive runs on the Mono Q columns and the active fractions from these runs were pooled prior to gel filtration. The active fractions from the Superose 6 column were pooled, concentrated and used for subsequent experiments, as described below.

Assays

All enzymatic assays were linear, except where noted (see below). When present, ATP was 2 mM in assays. Unless otherwise stated, in all assays, 50 µl aliquots of the fraction from the column or of the purified protease (10 µg) were incubated in 200 µl containing 50 mM TRIS-HCl (pH 7.8), 10 mM MgCl$_2$, 1 mM DTT, and 5 µg of the radioactive proteins, 0.5 µg of Ub-conjugates, or 0.5 mM of the fluorogenic peptide. For assays of proteolysis, the reaction mixtures contained approximately 15,000 cpm of Ub-lysozyme or labeled proteins. Degradation of $^{125}$I-lysozyme, Ub-$^{125}$I-lysozyme, $^{14}$C-casein, $^{14}$C-hemoglobin and OH/O$_2$$^-$ treated $^{14}$C-hemoglobin were assayed by measuring the production of acid-soluble radioactivity after 60 min of incubation at 37° C. Ub-$^{125}$I-lysozyme was prepared using liver fraction II, according to the method of Hough and Rechsteiner. Hough et al., *J. Biol. Chem.* 261:2400–2408 (1986), Hough, R. and Rechsteiner, M. *J. Biol. Chem.* 261:2391–2399 (1986). $^{125}$I-lysozyme and Ub were prepared as described previously. Waxman et al., *J. Biol. Chem.* 262:2451–2457 (1987), Fagan et al., *BioChem. J.* 243:335–343 (1987). The concentration of conjugates was calculated based on the specific radioactivity of the $^{125}$I-lysxozyme used for conjugate synthesis. One unit of sLLVT-MCA represents 10 nmol of MCA produced in 30 min.

Electrophoresis

Proteins were analyzed by SDS-PAGE (10% polyacrylamide gels), as described by Laemmli. Laemmli, U. K. *Nature (London)* 227:680–685 (1970). The gel was stained with Coomassie Brilliant Blue R-250. Non-denaturing gels were performed as previously described. Driscoll, J. and Goldberg, A. L. *J. Biol. Chem.* 265:4789–4792 (1990).

Immunological Methods

Immunoprecipitations were performed by incubation of anti-proteasome IgG (100 µg) with protein A-Sepharose, as previously described. Matthews et al., *Proc. Natl. Acad. Scii. USA* 86:2597–2601 (1989). Control immunoprecipitations were performed using Hyclone and the anti-Golgi monoclonal 53FC3. The monoclonal antibodies 2–24 against the purified human liver proteasome (Laemmli, U. K. *Nature* (London) 227:680–685 (1970)) were kindly provided by K. Tanaka and A. Ichihara (University of Tokushima, Japan). Polyclonal antibodies against purified human liver proteasome were raised in rabbits by T. Edmunds and A. L. Goldberg. Matthews et al., *Proc. Natl. Acad. Sci. USA*, 86:2597–2601 (1989). For immunoblotting, proteins were electrophoresed on a 10% SDS-polyacrylamide gel. After transferring the proteins to nitrocellulose sheets, (Hershko et al., *Proc. Natl. Acad. Sci. USA*, 77: 1783–1786 (1980)) immunoblots were performed as previously described. Hough et al., *J. Biol. Chem.*, 262:8303–8313 (1987), Hough et al., in *Ubiquitin* (Rechsteiner, M., ed.) pp. 101–134, Plenum Press, New York (1988).

Results

Isolation of Multipain

In the present experiments, the substrate used was $^{125}$I-lysozyme conjugated to Ub, which was prepared as described by Hough and Rechsteiner (Hough et al., *J. Biol. Chem.* 261:2400–2408 (1986), Hough, R., and Rechsteiner, M. *J. Biol. Chem.* 261:2391–2399 (1986)) but using liver extracts. Although this ubiquitinated protein was degraded only slowly in crude extracts, fraction II (the fraction that binds to DEAE-cellulose and contains the ATP-dependent degradative system) hydrolyzed this substrate rapidly to acid-soluble products (Table I). This process was linear for 2 h and stimulated 2- to 3-fold by the addition of 3 mM ATP. By contrast, the nonhydrolyzable ATP analogs, AMP-CPP or AMP-PNP, or ATP in the absence of Mg$^{2+}$ (and in the presence of 1 mM EDTA) did not stimulate the degradation of Ub-conjugated proteins.

TABLE I

PURIFICATION SCHEME FOR THE 500 kDA PROTEASE FROM RABBIT SKELETAL MUSCLE WHICH DEGRADES UBIQUITINATED LYSOZYME

| Fraction | Total protein (mg) | Specific activity (cpm/h × mg) +ATP | Specific activity (cpm/h × mg) −ATP | ATP stimulation (+ATP/−ATP) |
|---|---|---|---|---|
| Crude extract | 17433 | 82 | 74 | 1.1 |
| DE52 eluate (Fraction II) | 1170 | 779 | 338 | 2.3 |
| 0–38% (NH$_4$)$_2$SO$_4$ pellet | 392 | 2540 | 731 | 3.5 |
| Mono Q | 6.6 | 99433 | 20836 | 4.8 |
| Superose 6 | 2.6 | 209500 | 63723 | 4.7 |

Because of the limited capacity of the Mono Q column, there had to be three independent runs of the materials obtained from DE52. The active fractions from each run were combined prior to gel filtration, as described in Example 1.

To isolate the activity degrading the Ub-conjugates, fraction II was subjected to ammonium sulfate precipitation. At 38% (NH$_4$)$_2$SO$_4$ saturation, most of the proteasome complex remained soluble. Waxman et al., J. Biol. Chem. 262:2451–2457 (1987), Driscoll, J., and Goldberg, A. L. J. Biol. Chem. 265:4789–4792 (1990). The pelleted proteins were resuspended, dialyzed, and chromatographed on a column using Mono Q-FPLC (Pharmacia). Two peaks with Ub-$^{125}$I-lysozyme-degrading activity were found (FIG. 1). A small peak was eluted at approximately 100 mM NaCl and a second peak, which had more activity, at 240 mM. Peak 1 also showed appreciable degradative activity against lysozyme and casein, and this process also was stimulated almost 5-fold by ATP (FIG. 1). Upon gel filtration on Superose 6 (FPLC), it showed an apparent molecular weight between 1000 and 1500 kDa. Thus, it may correspond to the undissociated UCDEN or megapain complex. However, it is noteworthy that this structure degrades non-ubiquitinated lyxozyme perhaps as readily as it degrades the Ub-conjugated protein.

In addition to hydrolyzing Ub-lysozyme, peak 2 displayed ATP-stimulated degradation of lysozyme, but this latter activity was less than that in peak 1. Peak 2 also showed strong proteolytic activity against hemoglobin (Hb) damaged by exposure to .OH and .O$_2$ radicals generated by $^{60}$Co radiation. The hydrolysis of the oxidant-damaged hemoglogin was much more rapid than that of native Hb. Furthermore, degradation of the oxidant-damaged HB was independent of ATP. Previously, it was found that in red cells, oxidant-damaged hemoglobin is also degraded rapidly by a process not requiring ATP or the proteasome. However, peak 2 showed very little or no activity against $^{14}$C-casein or several oligopeptides, all of which are substrates for the proteasome, including succinyl-Ley-Leu-Val-Tyr-MNA succinyl-Phe-Leu-Phe-MNA (MNA is an abbreviation for methyl-naphthylamine), Z-Gly-Pro-MCA, Z-Ala-Arg-Arg-MNA, Z-Leu-Leu-Glu-βNA, glutaryl-Ala-Ala-Phe-MNA, Arg-Arg-MNA and Z-Gly-Gly-Arg-MNA.

Two peaks with ATP-stimulated activity against sLLVT-MCA were found. Peak 3, which eluted at about 320 mM, showed ATP-stimulated activity against sLLVT-MCA, lysozyme and casein, and ATP-independent degradation of native or .OH/O$^{2-}$-treated hemoglobin. Upon gel filtration on Superose 6 (FPLC), this peak was eluted with an apparent molecular weight of approximately 300kDa. This activity may represent a new protease or more likely a fragment of the proteasome. Peak 4 was found at 430 mM, which is normally where the proteasome is eluted when the 38–80% ammonium sulfate precipitable fraction is run on the same Mono Q column. Thus, in its Mr (600 KDa) and ability to hydrolyze sLLVT-MCA, peak 4 resembles the proteasome, but it did not degrade proteins (lysozyme, casein or hemoglobin) for reasons that are uncertain.

Figure 2:
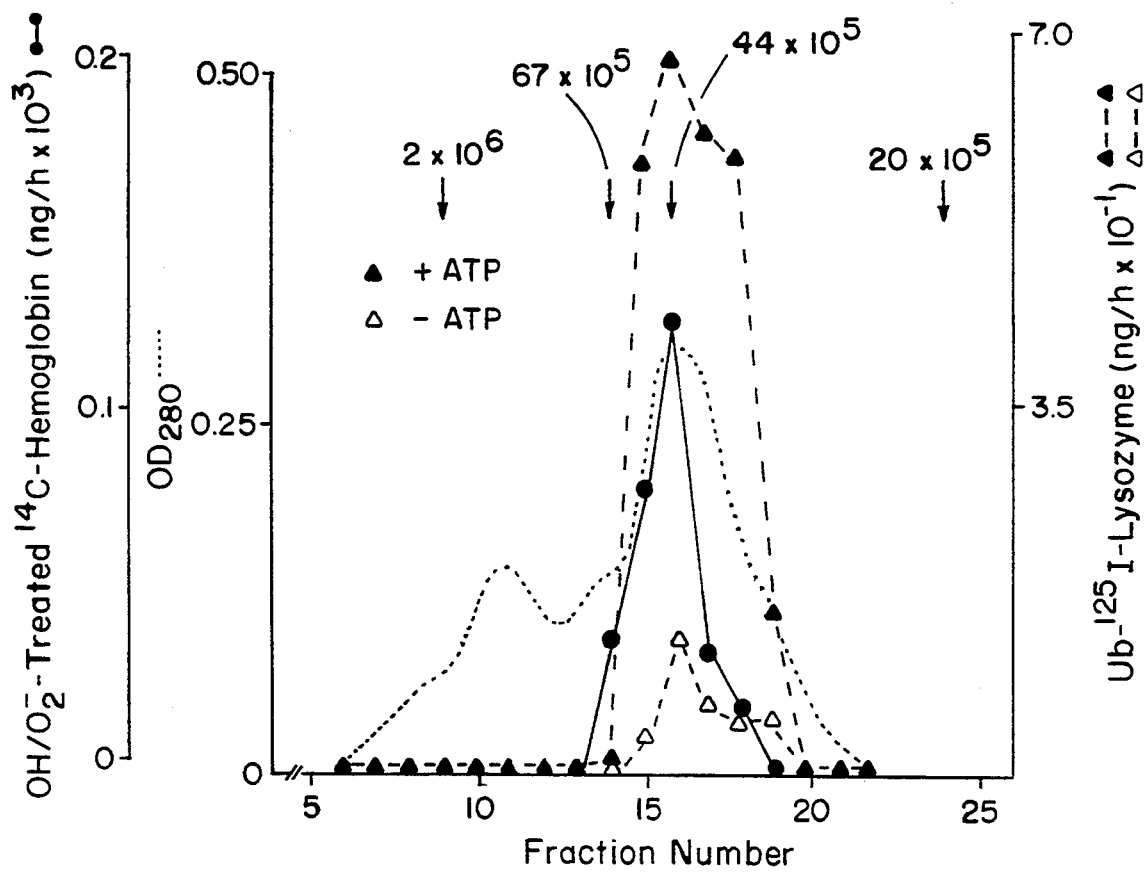

Subsequent work focused on peak 2, since it accounted for most of the ATP-stimulated breakdown of ubiquitinated lysozyme, and had strong activity against oxidant-damaged hemoglobin, but showed little activity against the sLLTV-MCA, a characteristic substrate of the proteasome. This activity was further purified by gel filtration using a Superose 6 gel filtration column, which yielded a single active peak with a molecular mass of approximately 440,000 (FIG. 2). Upon analytic gel filtration on Sepharose 300, it showed an apparent molecular weight of 540 kDa.

Figure 3:
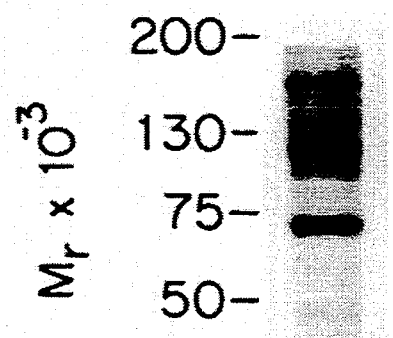

The steps used for rapid isolation of the major protease with Ub-conjugate degrading activity are summarized in Table 1. To assess its purity, the ATP-stimulated peak was subjected to PAGE under nondenaturing conditions. On a nondenaturing gel, it migrated as a single band significantly further (10–15 mm) than did the purified proteasome. (See Example 2). Upon SDS-PAGE analysis, the purified protease showed a set of at least 5 major subunit bands with Mr values between 50,000 and 150,000 (FIG. 3), and did not contain any of the 20–30 kDa bands characteristic of the proteasome. Previously, Hough et al. reported that SDS-PAGE analysis of the very large conjugate-degrading complex from reticulocytes revealed at least 6 to 10 high-molecular weight subunits (between 45 and 116 kDa), and Waxman et al. also observed 10 to 12 major polypeptides ranging between 43 and 110 kDa in partially purified preparations. Thus, the new protease appears to have subunits that are contained within the very large comples. (See Example 2).

Catalytic Properties of the 500 kDa Enzyme

After gel filtration (FIG. 2), the 500 kDa peak showed the same activities as after Mono Q chromatography. Hydrolysis of Ub-lysozyme was stimulated 5-fold by addition of 2 mM ATP and degradation of lysozyme 3-fold. On the other hand, degradation of native and oxidant-damaged hemoglobin were both independent of ATP (as in crude extracts) and the oxidant-treated substrate was degraded 15 times faster than native hemoglobin. With these substrates, as with Ub-$^{125}$I-lysozyme and $^{125}$I-lysozyme, the enzyme showed a sharp pH optimum of 7.8. The activity decreased by about 50% at pH 7.0 or 10.0, and no activity was evident below pH 5.0 or above 12.0.

Due to difficulties in preparation of large amounts of Ub-conjugated proteins, the concentration of ubiquitinated lysozyme used in the standard assays was about 10 times lower than that of free lysozyme (when the molar amounts of the $^{125}$I-lysozyme were compared). Nevertheless, the new protease degraded the ubiquitinated lysozyme almost as rapidly as it degraded nonubiquitinated ones (Table II).

TABLE II

EFFECT OF INNUMOPRECIPITATION WITH ANTI-PROTEASOME MONOCLONAL ANTIBODY ON DEGRADATION OF DIFFERENT SUBSTRATES BY THE PROTEASOME AND THE NEW PROTEASE

| | Lysozyme | | Ubiquitinated lysozyme | | Casein (ng/h) | |
|---|---|---|---|---|---|---|
| | −ATP | +ATP | −ATP | +ATP | −ATP | +ATP |
| PROTEASOME | | | | | | |
| Control Antibody | 612 | 1872 | 7 | 8 | 217 | 856 |
| Anti-Proteasome Antibody | 41 | 105 | 0 | 0 | 32 | 74 |
| NEW PROTEASE | | | | | | |
| Control Antibody | 79 | 292 | 41 | 190 | 0 | 0 |
| Anti-Proteasome Antibody | 70 | 281 | 36 | 179 | 0 | 0 |

| | Hemoglobin | | $OH/O_2$-treated hemoglobin | | SLLVT-MCA (units) | |
|---|---|---|---|---|---|---|
| | −ATP | +ATP | −ATP | +ATP | −ATP | +ATP |
| PROTEASOME | | | | | | |
| Control Antibody | 45 | 51 | 927 | 886 | 0.8 | 3.7 |
| Anti-Proteasome Antibody | 0 | 0 | 31 | 36 | 0.1 | 0.1 |
| NEW PROTEASE | | | | | | |
| Control Antibody | 19 | 17 | 263 | 270 | 0.1 | 0.2 |
| Anti-Proteasome Antibody | 15 | 22 | 267 | 256 | 0.1 | 0.1 |

Figure 4:
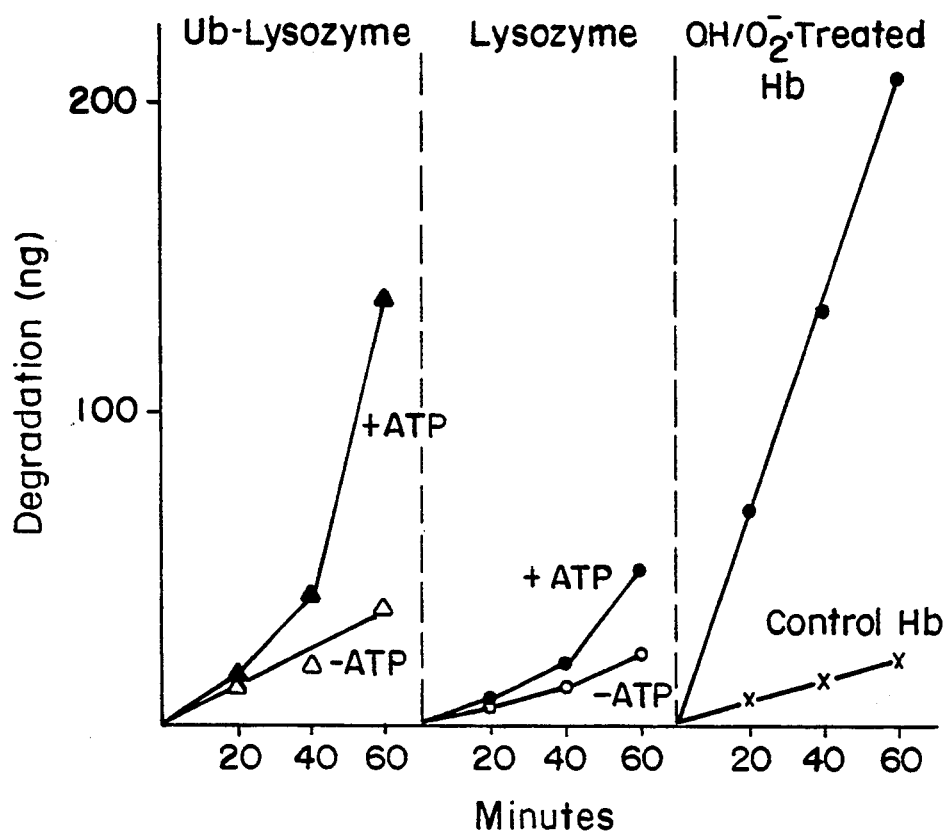
FIG. 4 is a graphic representation of the relative rates of hydrolysis of lysozyme, ubiquitinated lysozyme, hemoglobin and oxidant-damaged hemoglobin by the 500 kDa protease.

When the two forms of lysozyme were present at the same concentrations, Ub-$^{125}$I-lysozyme was degraded about 3-fold faster than $^{125}$I-lysozyme (FIG. 4). These findings indicate a clear preference of the new protease for the ubiquitinated substrate, in contrast to the proteasome, which showed very little, if any, activity against the Ub-conjugate. To define the nature of the proteolytic reaction, the size of the acid-soluble products generated by this protease from Ub-$^{125}$I-lysozyme was determined. Upon chromatography on a G25 gel filtration column (equilibrated with 0.2M Na-acetate and 0.1M NaCl), the acid-soluble pieces eluted as a single sharp peak with an approximate molecular weight of 1,300 D, as defined by the marker peptide, substance P. Thus, the enzyme is an endopeptidase and seems to lack exopeptidase activity.

In order to test whether this new protease shared common components with the proteasome, a monoclonal antibody against the human liver particle (Matthews et al., *Proc. Natl. Acad. Sci. USA*, 86:2597–2601 (1989) Table II) or a polyclonal antibody against the rat liver proteasome was used. Immunoprecipitation with either antibody did not affect the activity of the new enzyme when assayed against lysozyme, Ub-lysozyme, or oxidant-treated hemoglobin, although these treatments quantitatively precipitated the purified rabbit muscle proteasome, as assayed with $^{14}$C-casein or sLLVT-MCA (Table II). (These various proteasome activities are not directly inhibited by the antibodies, but in these experiments, these activites were removed together by precipitations with protein A-Sepharose). The absence of cross-reactivity between these two multimeric proteases was confirmed by Western blot, where these monoclonal or polyclonal antibodies failed to react with the new protease.

Nucleotide Effects

Table III presents the effects of nucleotides on the degradation of Ub-$^{125}$I-lysozyme by the new activity from skeletal muscle. In these assays, the active peak from the Suparose 6 chromatography was incubated with Ub-$^{125}$I-lysozyme at 37° C. for 1 hour. The reaction mixtures contained 2 mM of the nucleotides or 10 mM PPi. As shown in Table III, the hydrolysis of Ub-$^{125}$I-lysozyme by the purified enzyme was stimulated up to 7-fold by ATP. In contrast, ADP or AMP or inorganic phosphate had no significant effect on this process. No stimulation was seen with the nonhydroyzable ATP analogs, adenyl 5′-oyl-imidodiphosphate (AMP-PNP) and adenosine 5′-o-thiotriphosphate (ATP-γ-S). Therefore, this reaction seems to require ATP hydrolysis, as has been shown for the ATP-cleaving proteases, La (lon) and Ti (clp) from *E. coli*, and mitochondria, as well as the rapidly isolated form of the proteasome.

TABLE III

EFFECT OF NUCLEOTIDES ON THE DEGRADATION OF Ub-$^{125}$I-LYSOZYME BY THE NEW ACTIVITY FROM SKELETAL MUSCLE

| Compound | Relative activity (%) |
|---|---|
| None | 100 |
| ATP | 743 |
| ADP | 113 |
| AMP | 130 |
| AMP-PNP | 90 |
| ATP-γ-S | 103 |
| CTP | 373 |
| GTP | 435 |
| UTP | 108 |
| PPi | 118 |

Reaction mixtures contained 2 mM of the nucleotides or 10 mM PPi.

In the absence of ATP, the hydrolysis of Ub-conjugates by the purified enzyme was linear for at least 2 h and was stimulated many fold when ATP was added (FIG. 4). Therefore, this effect involves a real activation through ATP hydrolysis, rather than simply a stabilization of the enzyme. It is also noteworthy that a lag period of about 20 min preceded the activation by ATP of the degradation of both ubiquitinated and non-ubiquitinated lysozme (FIG. 4). This interesting lag period is clearly related to the stimulating effect of ATP, since no lag time was seen for the ATP-independent breakdown of these substrates or of oxidant-damaged hemoglobin, which was a linear process. The basis for this intriguing time dependence is unclear, but it seems to be due to loss of some additional component. Similar effects have not been observed for other ATP-dependent proteolytic enzymens in eukaryotic or prokaryotic cells.

The requirement for ATP could also be satisfied in part by CTP or GTP, which caused approximately a 4-fold stimulation of protein breakdown (Table III). This nucleotide requirement thus resembles prior findings for the nucleotide specificity for Ub-conjugate degradation by the 1500 kDa complex. These nucleotide effects also differ from those required by the ATP-dependent form of the proteasome, in which any nucleotide triphosphate, including nonhydrolyzable analogs, could activate hydrolysis of peptide substrates, but the stimulation of protein breakdown was only seen with ATP.

When different ATP concentrations were studied, a maximal stimulation of conjugate degradation was observed with 1 mM. The data suggested a $K_m$ for ATP of 0.5 mM or less, which is well below intracellular ATP concentration. Thus, this activation appears to be physiological, and this $K_m$ is consistent with earlier observations on cultured cells, where depletion of cellular ATP blocks protein breakdown only when ATP levels are reduced drastically (>75%).

The enzyme itself is quite labile. When stored at 40° C. in the absence of ATP, there is a progressive loss of proteolytic activity against the Ub-conjugates. Even at −70° C., the abilities to degrade Ub-conjugated lysozyme, nonubiquitinated lysozyme, or oxidant-damaged hemoglobin all decreased together by 50% in 3–4 days. This rapid inactivation could be prevented by the presence of ATP or the nonhydrolyzable analog, AMP-PNP. Addition of glycerol, which stabilizes the ATP-dependent degradative system in crude extracts and the proteasome, also prevented the progressive loss of this activity and left the enzyme fully functional after 6 days. This ability of nucleotides and glycerol to stabilize the enzyme was also observed at 40° C., where inactivation was even more rapid. The ATP-dependent form of the proteasome is also labile and is stabilized by nucleotides; however, the instability of these two protease complexes are quite different. With time the proteasome loses its ATP dependence and becomes spontaneously active, unlike the new enzyme, which simply loses activity in the absence of ATP. In addition, detergents, such as SDS or fatty acids, which stimulate the proteasome, inactivate the new enzyme (Table IV), which appears to be a much more labile structure.

TABLE IV

EFFECT OF INHIBITORS ON DIFFERENT ACTIVITIES OF THE NEW PROTEASE AND ON THE PROTEASOME FROM SKELETAL MUSCLE

| | NEW PROTEASE | | | PROTEASOME SLLVT-MCA |
|---|---|---|---|---|
| Addition | Ub-lysozyme | lysozyme | OH/O$_2$-treated hemoglobin | |
| | Relative activity (%) | | | |
| None | 100 | 100 | 100 | 100 |
| DEP (1 mM) | 96 | 92 | 91 | 18 |
| Cystatin A (4 uM) | 30 | 24 | 27 | 93 |
| Hemin (0.1 mM) | 0 | 0 | 7 | 0 |
| NEM (1 mM) | 29 | 27 | 30 | 37 |
| Leupeptin (0.1 mM) | 69 | 72 | 73 | 83 |
| E64 (0.1 mM) | 100 | 100 | 100 | 100 |
| NaOleate (0.125 mM) | 29 | 34 | 40 | 179 |
| SDS (0.01%) | 44 | 46 | 42 | 125 |
| o-Phenanthroline (0.1 mM) | 48 | 55 | 54 | 60 |

The new protease was incubated at 37° C. for 1 h with the protein substrates and 2 mM ATP. The proteasome obtained by Superose 6 chromatography was incubated with sLLVT-MCA. Mixtures were preincubated for 10 min at 20° C., prior to addition of the substrate. DFP was dissolved in DMSO, whose final concentration (1%) did not affect enzyme activities.

Actions of Inhibitors

To characterize further the new ATP-dependent protease, the effects of various types of enzyme inhibitors were tested (Table IV). Diisopropylfluorophosphate (DFP), an irreversible inhibitor of serine proteinases did not affect conjugate breakdown. o-Phenanthroline, which chelates heavy metals, showed some inhibition. In contrast, N-ethylmaleimide (NEM), a thiol-blocking reagent, and egg-white cystatin (cystatin A), a potent inhibitor of many papain-like thiol proteinases, strongly inhibited this activity. A similar inhibition was observed with the related human polypeptide Stefin A. A similar effect of cystatin was previously reported for the ATP+Ub-dependent proteolysis against the very large UCDEN complex from rabbit muscle. The inhibition by Stefin A is physiologically interesting, since homologous protein inhibitors are present in many mammalian tissues. At similar concentrations, cystatin B showed a 55% inhibition, and no significant effect was detected by cystatin C. Although this new activity thus appears to be a thiol protease, it was only inhibited by 30% in the presence of leupeptin and not at all by E64, both inhibitors of many thiol proteinases (e.g. lysosomal enzymes or calpains). However, the susceptibility to leupeptin and E-64 is strongly influenced by the sequences preceding the sessile bond and not all thiol proteases are sensitive to them. Hemin, which can inhibit completely the ATP-Ub-dependent proteolytic system and the proteasome, also blocked conjugate-degrading activity by the new protease (Table IV).

These findings suggest that the new enzyme has a thiol residue in its active site. Accordingly, dithiothreitol promoted its activity and was necessary for maintaining the enzyme function. The pattern of effective inhibitors clearly differentiates this activity from the proteasome, which when activated acts as a serine protease (Table IV) with multiple catalytic sites (although it also has essential sulfhydryl groups). As shown in Table IV, the effects of the different inhibitors on the degradation of $^{125}$I-lysozyme and ·OH/OY$^{2-}$-treated $^{14}$C-hemoglobin were also compared. Very similar inhibitory profiles were obtained with these substances, as was found with Ub-lysozyme. Thus, it seems most likely that a single type of active site is involved in the hydrolysis of these different types of proteins.

Although degradation of oxidant-damaged hemoglobin was independent of ATP, while breakdown of ubiquitinated and nonubiquitinated lysozyme required nucleotide hydrolysis, a single enzyme complex seems responsible for degrading all three substrates for several reasons: a) These 3 activities copurified (FIGS. 1 and 2). b) ATP and glycerol stabilized all three in a similar fashion. c) The different activities had similar pH optimum. d) The ability of cystatin and other inhibitors to reduce the degradation of Ub-conjugates correlated with their ability to inhibit breakdown of the other proteins. The simplest interpretation of these data would be that all three substrates are degraded by a single active site or a single type of site, even though it is hard to understand why ATP promotes breakdown of some but not all substrates.

To test if ubiquitinated and nonubiquitinated proteins were bound to the same site, the purified enzyme was incubated for 1 h at 37° C. in the presence of saturating concentrations (5 to 25 μg) of lysozyme, hemoglobin, or oxidant-treated hemoglobin. None of these substrates reduced the degradation of Ub-$^{125}$I-lysozyme (containing 0.5 μg of lysozyme), even though the nonlabelled lysozyme and oxidized hemoglobin decreased linearly the breakdown of the homologous radioactive proteins. In addition, no competition was detected between lysozyme and oxidant-treated hemoglobin at these concentrations. This failure to demonstrate competition between those 3 substrates suggests that the protease has specific binding domains that recognize these different protein substrates and also that Ub-lysozyme breakdown does not involve generation of free lysozyme.

Association with the Proteasome

Because of its ability to degrade Ub-conjugated lysozyme, the enzyme could be a component of the 1500kDa UCDEN complex. In fact, the new enzyme resembles in its size and chromatographic behavior component "CF-1" from reticulocytes. If so, it should form a complex with the proteasome in the presence of ATP. To test this hypothesis, approximately equal amounts of multipain and extensively purified proteasome isolated from muscle were incubated at 37° C., with or without $Mg^{2+}$-ATP. Active peaks (1 mg protein each) obtained after Superose 6 gel filtration were incubated together in the presence of 1 mM Mg ATP for 30 minutes and then applied to the same Superose 6 column. Fractions of 1.0 ml. were collected at a flow rate of 0.1 ml./min. Samples were assayed for Ub-$^{125}$I-lysozyme.

Figure 5:
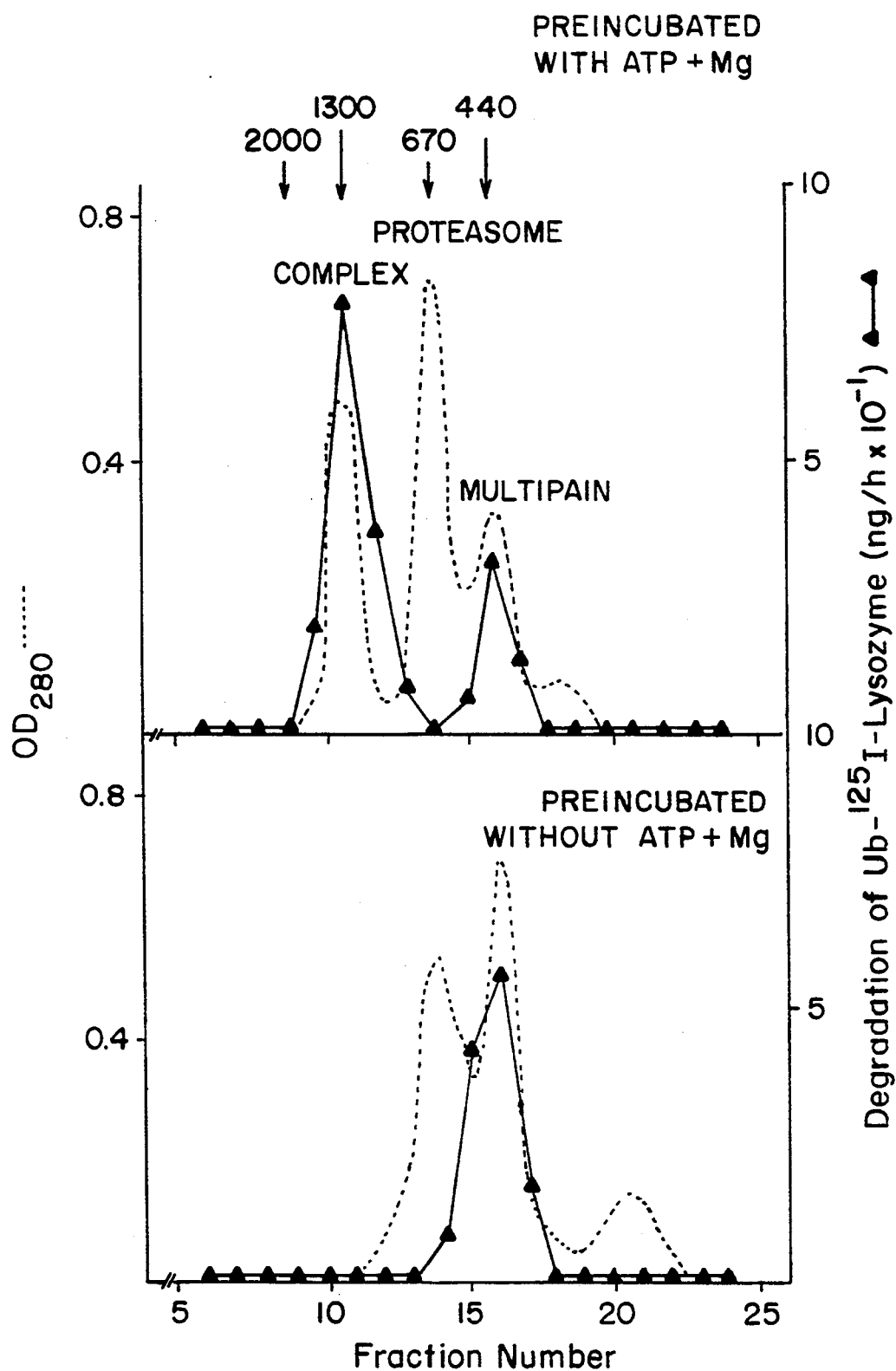
FIG. 5 is a graphic representation of formation of a 1300 kDa multienzyme complex following preincubation of the proteasome and the multipain with MgATP. Molecular weight markers used were blue dextran, phosphorylase kinase, thyroglobulin, ferritin and β-amylase.

As shown in FIG. 5, preincubation in the presence of $Mg^{2+}$-ATP allowed formation of a 1300kDa complex that also degrades ubiquitinated lysozyme. Omission of ATP or $Mg^{2+}$ (FIG. 5), or substitution of ATP by the analog AMP-PNP, prevented complex formation and also led to some breakdown of the 500 and 700kDA enzymes. If the proteasome was not included, no change in the size of the multipain activity occurred upon incubation with $Mg^{2+}$-ATP (data not shown). These observations also confirm that the multipain preparations must be free of proteasome, as was suggested by the SDS-PAGE and Western Blot analysis, and also indicate that the time-lag in activation by ATP (FIG. 4) is not due to intermolecular associations.) Finally, the Ub-conjugate-degrading activity formed in vitro could be blocked by immunoprecipitation with anti-proteasome antibodies, as in previous studies with the native complex.

EXAMPLE 2

Assessment of Complex Formation Between the Proteasome and Multipain and Properties of the Complex Experimental Procedures Substrates ($^{125}$I-lysozyme, ubiquitinated $^{125}$I-lysozyme, $^{14}$C-methyl-hemoglobin, and $^{14}$C-methyl-hemoglobin damaged by OH and $O_2$ radicals) were prepared as described in Example 1.

Fractionation of muscle extracts— The psoas muscles were excised from New Zealand White (4–5 kg) male rabbits (Millbrook Farms, Mass.), and post-mitochondrial extracts were prepared and fractionated on DEAE-cellulose, as described in Example 1. The proteins absorbed to DEAE-cellulose and eluted with 0.5M NaCl (Fraction II) were subjected to (NH4)2SO4 fractionation in order to separate the free proteasome (38–80%) from other activities (0–38%). Both fractions were concentrated and applied separately to a Pharmacia Mono Q column (FPLC). Proteasome and multipain fractions were further applied to a Pharmacia Superose 6 gel filtration column, and the active fractions were pooled and used for subsequent experiments.

Assays

Degradation of $^{125}$I-lysozyme, Ub-$^{125}$I-lysozyme, $^{14}$C-casein, $^{14}$C-hemoglobin and OH/O2-treated $^{14}$C-hemoglobin were assayed, as described in Example, 1 and by Tanaka and Co-Workers. Tanaka, K. et al., *J. Biol. Chem.*, 261:15197–15203 (1986). All assays were linear for two hours. Unless otherwise stated, the assays used 50 ul aliquots of the column fractions or of the purified proteases (5 μg) incubated in 200 μl containing 50 mM TRIS-HCl (pH 7.8), 10 mM $MgCl_2$, 1 mM DTT, and 5 μg of the radioactive proteins, 0.5 μg of $^{125}$I-lysozyme conjugates or 0.5 mM of the fluorogenic peptide, succinyl-Leu-Leu-Val-Try-7-amido-4-methyl-coumarin (sLLVTA-MCA). The amount of Ub-conjugates was calculated based on the specific radioactivity of the $^{125}$I-lysozyme bound to Ub. One unit of sLLVT-MCA represents 10 nmol of MCA produced in 30 min.

Electrophoresis

Protein was assayed by the method of Bradford. (Bradford, M. M., *Anal. Biochem.* 72:248–254 (1976)). Proteins were analyzed by SDS-PAGE (10% polyacrylamide) using the method of Laemmli (Pickart, C. M. et al., *Arch. Biochem. Biophys.* 272:114–121 (1989)) and stained with Coomassie Brilliant Blue R-250. Non-denaturing electrophoresis in 4% polyacrylamide gels was run, as previously described in Example 1 and by Driscoll and Golberg. Driscoll, J. and A. L. Goldberg, *J. Bio. Chem.* 265:4789–4792 (1990).

Results

Complex Formation Between the Proteasome and Multipain

The ability of these two ATP-activated proteases to form a larger complex that degrades Ub-conjugates was further defined as follows. Multipain and proteasome fractions obtained by Superose 6 gel filtration were incubated in the presence or absence of ATP and $Mg^{2+}$ for 30 minutes at 37° C., and then loaded on the same gel filtration column. These conditions led to the conversion of most of the proteasome (700 kDa) and multipain (500 kDa) activities into a larger form that eluted at 1500 kDa. The larger peak showed ATP-activated hydrolysis of $^{125}$I-Ub-lysozyme, $^{125}$I-lysozyme, sLLVT-MCA and $^{14}$C-casein.

Omission of the ATP and $Mg^{2+}$ or supplying the non-hydrolyzable ATP analog, AMP-PMP in place of ATP completely prevented complex formation. These findings suggest that nucleotide hydrolysis is necessary for the association of the two enzymes. Both the proteasome and multipain were necessary for formation of the 1300 kDa complex; in fact, neither of these enzymes when incubated alone showed any tendency to form large complexes in the presence of ATP and $Mg^{2+}$. As isolated here, the activities of both the proteasome and multipain were quite labile upon storage, although ATP and glycerol did cause some stabilization. In the absence of ATP and $Mg^{2+}$, less total protease and peptidase activities were recovered from the column, and a rise in the ATP-independent was observed. Routinely, the Superose 6 gel filtration columns to isolate the large complex were run in buffer lacking ATP; nevertheless, the complex did not dissociate significantly, even upon repeated gel filtration. Thus, at 4° C., ATP must be required to maintain the association of proteasome and multipain.

A variety of observations suggest that multipain and the proteasome are present in equal amounts in the complex. For example, in the association reaction, if either the multipain or proteasome fraction was reduced by half, complex formation also decreased approximately in half, as would be expected for a complex with a specific composition. A 1:1 association would be consistent with the molecular size (1300–1500 kDa) obtained from gel filtration for the complex (700 kDa plus 500 kDa) and also with the SDS gel patterns.

Polypeptide Components of the 1500 kDa Complex

Multipain, when analyzed by SDS PAGE, contains at least 6 large polypeptides of 70–150 kDa, which are distinct from the many 20–30 kDa subunits of the proteasome. When the proteasome-multipain complex was analyzed upon SDS-PAGE (FIG. 6), it was found to contain all of the polypeptides present in purified multipain (i.e., 5 bands of 70–200 kDa), the recognized subunits of the purified proteasome (i.e. the bands between 20–30 kDa), as well as a number of polypeptides of 40–110 kDa. The latter polypeptides were also present in partially purified proteasome fraction (FIG. 6) and were incorporated into the 1500 kDa peak upon complex formation. These experiments used proteasomes purified by a lengthy combination of steps, including DEAE chromatography, $NH_4SO_4$ precipitation, Mono Q chromatography and Superose 6 gel filtration. Therefore, the 40–110 kDa polypeptides must have been rather tightly associated with the proteasome, since they had copurified with the 700 kDa particles at least through the filtration step.

An important observation was that when the proteasome fraction was purified further, by Affigel-blue chromatography, such that primarily 20–30 kDa subunits were found upon SDS PAGE, the proteasome obtained was unable to form a complex with multipain in the presence of ATP and $Mg^{2+}$. Thus, the Affigel-blue step seems to have removed some component(s), presumably one or more of the 40–110 kDa polypeptides, which are essential for complex formation.

Proteolytic Activities of the 1500 kDa Complex

Figure 7:
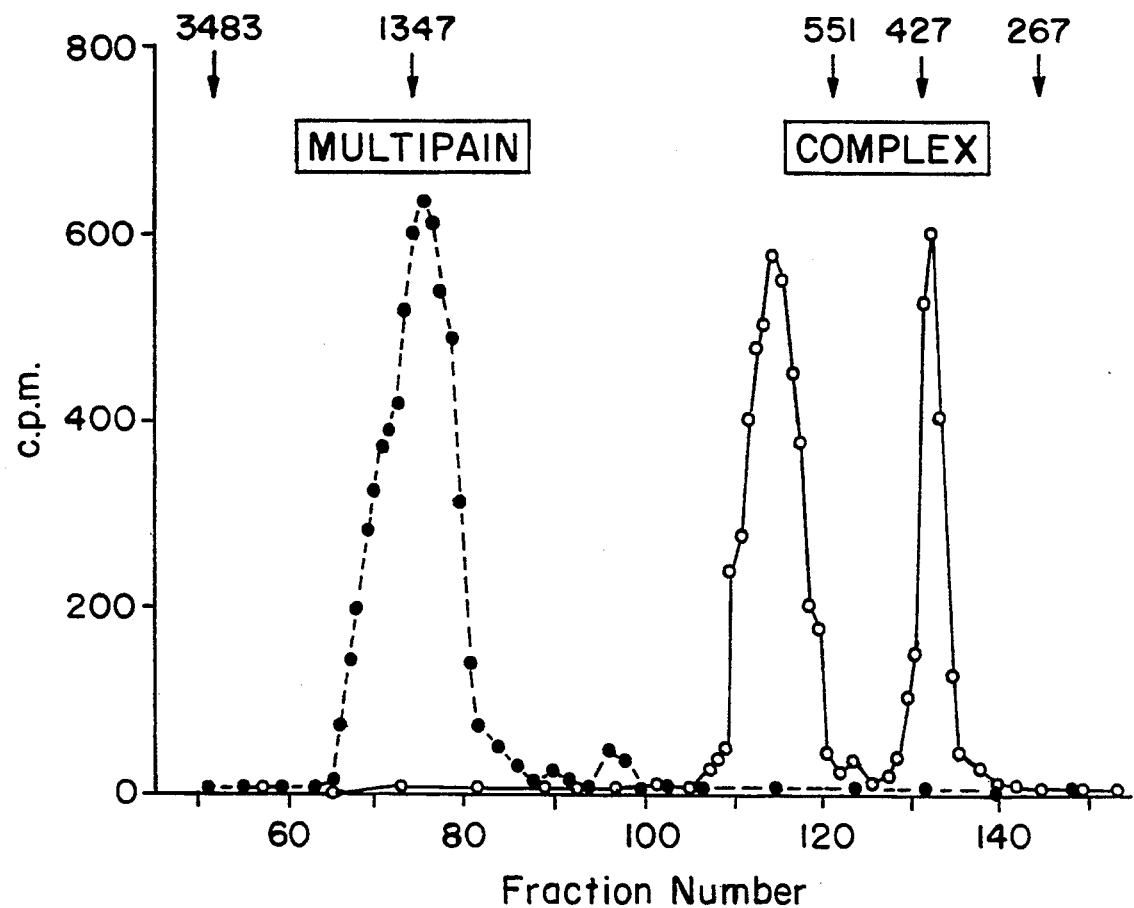
FIG. 7 is a graphic representation of acid-soluble $^{125}$I-products of Ub-$^{125}$I-lysozyme-conjugates degraded by multipain (●) or the complex formed upon incubation of the proteasome and multipain (○). The molecular-weight markers were substance P (1,347Da), ATP (551Da), ADP (427Da) and adenosine (267Da).

In addition to degrading Ub-lysozyme, the 1500 kDa complex degraded a variety of unconjugated protein substrates, as do multipain and the proteasome (Table V, FIG. 7).

TABLE V

COMPARISON OF THE RELATIVE ACTIVITIES OF THE PROTEASOME, MULTIPAIN AND THE COMPLEX AGAINST DIFFERENT SUBSTRATES

| Activity | Ubiquitinated Lysozyme* | Lysozyme | Casein (μg/h × nmol) |
|---|---|---|---|
| Proteasome | 0.3 | 56 | 24 |
| Multipain | 5 | 6 | 0 |
| Complex | 11 | 92 | 31 |

| Activity | .OH/$O_2^-$-treated Hemoglobin | Hemoglobin | sLLVT-MCA (units) |
|---|---|---|---|
| Proteasome | 1 | 30 | 133 |
| Multipain | 0.4 | 7 | 5 |
| Complex | 0.7 | 29 | 162 |

*All protein substrates were at 25 μg/ml except Ub-$^{125}$I-lysozyme, which was present at 2.5 μg/ml. (For $^{125}$I-Ub-lysozyme, this concentration refers to the amount of $^{125}$I-lysozyme present.)

Degradation rates in the presence of 2 mM ATP were calculated per nmol of enzyme using 670 kDA as the molecular weight for the proteasome, 500 kDa for multipain, and 1300 kDa for the complex.

ATP hydrolysis was required not only for complex formation, but also for maximal activity against most substrates. The degradation of Ub-$^{125}$I-lysozyme, $^{125}$I-lysozyme, sLLVT-MCA, or casein by the complex occurred at linear rates and was stimulated 3 to 5 fold by ATP (FIG. 7) or data not shown). Although breakdown of casein and lysozyme by the complex was stimulated by ATP, degradation of hemoglobin (a poor substrate) or of oxidant-damaged hemoglobin (a much better substrate) was not affected by ATP. The proteasome and multipain were also found to degrade oxidant-damaged hemoglobin (in contrast to these other substrates) by an energy-independent process, for reasons that are unclear. Thus, the complex showed all the enzymatic activities characteristic of both the proteasome and of multipain, including their activation by ATP.

Due to difficulties in preparation of large amounts of Ub-conjugates, the concentration of Ub-$^{125}$I-lysozyme used routinely in the assays was about 10 times lower in molar amounts than that of $^{125}$I-lysozyme (as defined by the molar amounts of lysozyme). When the free and conjugated forms of lysozyme were present at the same molar concentrations, multipain hydrolyzed Ub-lysozyme 2–4 times faster than it hydrolyzed the unconjugated substrate.

It is noteworthy that both lysozyme and ubiquitinated lysozyme were degraded about 2-fold faster by the complex than by equal molar amounts of multipain or of the proteasome (Table V). In fact, the rates of degradation of these substrates by the complex were significantly greater than the sum of the rates with the proteasome and multipain acting separately (Table V). Thus, in the complex, these enzymes function synergistically against lysozyme and ubiquitinated lysozyme (Table VI).

TABLE VI

MULTIPAIN AND PROTEASOME FUNCTION SYNERGISTICALLY IN DEGRADING Ub-LYSOZYME CONJUGATES

| Enzyme Added Initially | Degradation in 1st hour (ng) | Additions at 60 min | Degradation in 2nd hour (ng) |
|---|---|---|---|
| Multipain | 80 | None | 74 |
|  |  | Proteasome | 156 |
|  |  | Cystatin | 4 |
|  |  | Proteasome + Cystatin | 12 |
| Proteasome | 9 | None | 5 |
| Complex | 71 | None | 65 |
|  |  | Proteasome | 71 |
|  |  | Cystatin | 18 |

The data presented in Table VI was obtained under the following conditions: enzymes were added at equal molar amounts based on apparent molecular weights of 670 kDa, 500 kDa and 1300 kDa. Reaction mixtures contained 2 mM ATP and 500 ng of the radioactive substrate. When indicated, egg white cystatin was at 4 μM to inactivate multipain. Degradation of Ub-conjugates was assayed by measuring the production of acid-soluble radioactivity at 60 or 120 min of incubation at 37° C. Furthermore, when the proteasome fraction was added to multipain in the presence of ATP to allow complex formation (Table VI), together they degraded ubiquitinated lysozyme much faster than when multipain acted alone, or when multipain and then the proteasome fraction acted sequentially on this substrate (Table VI). In this experiment, complex formation led to twice the degradation as with multipain alone. Also, if proteasome was added to multipain, but the multipain was inactivated with cystatin, little or no further production of acid-soluble counts occurred beyond what was catalyzed by multipain in the previous hour. Thus, the synergistic action of the 500 kDa and 700 kDa enzymes was evident only when complex formation occurred.

Although the addition of the proteasome fraction to multipain caused much greater degradation of Ub-lysozyme than with multipain alone (Table VI), the addition of DFP-inactivated proteasome did not enhance the breakdown of Ub$^{125}$I-lysozyme, even though under these conditions complex formation did occur, as shown by gel filtration. Proteolytic activity thus does not appear necessary for complex formation, and within the complex, multipain and proteasome act synergistically, provided both components are enzymatically active. It is also noteworthy that addition of excess proteasome to the isolated complex (i.e. equal molar amount of the 700 and 1500 kDa particles) caused no further enhancement of Ub-conjugate degradation (Table VI). Thus, proteasome-associated peptidases do not seem to degrade either Ub-conjugates or the products of multipain activity significantly unless in association with multipain in a definite stoichiometric relationship.

Products of Degradation of Ub-lysozyme

The peptide products of the Ub-$^{125}$I-lysozyme degradation were also analyzed to see if complex formation by multipain alters the extent of (in addition to the rate of) proteolysis. After incubation of the substrate with multipain or the complex, the acid-soluble radioactive products were subjected to gel filtration on Sepharose G-25. As shown in FIG. 7, multipain, in hydrolyzing Ub-$^{125}$I-lysozyme, generates a single sharp peak of radioactivity. On gel filtration, it coeluted with substance P, a linear peptide, which has a molecular weight of 1347 Da. However, when the 1500 kDa complex catalyzed Ub-lysozyme degradation, no $^{125}$I was eluted at this size. Instead, all radioactivity was found in two smaller peaks of approximately 600 and 400 kDa (i.e. in peptides containing about 5 and 3 residues). These findings strongly suggest that the peptidase function of the proteasome is essential to complete the degradation of Ub-lysozyme initiated by multipain. Furthermore, as was also demonstrated in Table VI, both enzymes must be present simultaneously to allow their coordinate function. Thus, when multipain was incubated with Ub$^{125}$I-lysozyme and then its activity was inhibited by cystatin (as shown in Table VI), the addition of proteasome did not cause further degradation of the acid-soluble peptides produced by multipain. Thus, to be effective in degrading the peptide produced by multipain, the proteasome must be present in the complex with it.

Effect of Inhibitors

As is evident from the data presented below, the 1500 kDa complex is sensitive to inhibitors of both the proteasome and multipain functions.

To characterize further the 1500 kDa complex, the effects of various inhibitors of the component enzymes were tested. This was done under the following conditions: enzymes were incubated with Ub-$^{125}$I-lysozyme (complex or multipain) or with SLLVT-MCA (proteasome) in the presence of compounds indicated in Table VII. Assays contained 2 mM ATP. Reaction mixtures were incubated for 10 min at 20° C. prior to the addition of the substrate. DFP was dissolved in DMSO. The final concentration of DMSO was 1.0%, which did not affect conjugate breakdown. The data for multipain and the proteasome were obtained under the same experimental conditions. As shown in Table VII, the isolated complex is sensitive to inhibitors of both the proteasome and multipain functions. Diisopropylfluorophosphate (DFP), an irreversible inhibitor of serine proteases and of proteasome and o-phenanthroline, which chelates heavy metals, inhibited conjugate breakdown by about 60%. This latter observation suggests that a metalloproteinase may also be present in the very large complex.

TABLE VII

COMPARISON OF THE EFFECTS OF INHIBITORS ON THE PROTEOLYTIC ACTIVITIES OF THE COMPLEX, MULTIPAIN AND THE PROTEASOME

| Compound | Complex (Ub-$^{125}$I-Lysozyme) | Multipain | Proteasome (sLLVT-MCA) |
|---|---|---|---|
| | Relative Activity (%) | | |
| None | 100 | 100 | 100 |
| DFP (1 mM) | 38 | 96 | 18 |
| Cystatin (4 μM) | 35 | 30 | 93 |
| NEM (1 mM) | 33 | 29 | 37 |
| Leupeptin (100 μM) | 75 | 69 | 83 |
| E-64 (100 μM) | 96 | 100 | 100 |
| Sodium oleate (125 μM) | 38 | 29 | 179 |
| SDS (0.01%) | 46 | 44 | 125 |
| o-Phenanthroline (100 μM) | 57 | 48 | 60 |

The effects of the inhibitors against the complex were compared with their effects on multipain and proteasome separately (see Table VII). N-ethylmaleimide (NEM), a thiol-blocking agent, and egg-white cystatin (cystatin A), a potent inhibitor of many papain-like thiol proteinases, retarded the activity of the complex by 65%. A similar inhibition by cystatin of ATP-Ub-dependent proteolysis was previously reported for the UCDEN complex isolated from rabbit muscle. Fagan, J. M., et al., Biochem. J., 243:335–343 (1987). Other inhibitors of thiol proteases, like leupeptin or E64, did not show any significant effect on the complex, as expected from their inability to inhibit the proteasome or multipain.

It is noteworthy that the complex is sensitive to inhibitors of both the proteasome (e.g., DFP) and of multipain (e.g. cystatin A). Thus, it behaves as both a serine protease and a thiol protease. Detergents, such as SDS or fatty acids (oleate) were previously noted to activate the proteasome (Hough, R., et al., J. Biol. Chem., 262:8303–8313 (1987)) and were shown to inhibit multipain. Both these agents inhibited the function of the complex. Thus, Ub-conjugate breakdown by the complex requires the function of both component proteases. Moreover, these various findings together suggest that multipain initiates the degradation of Ub-conjugates, while the proteasome completes it (Table VI and FIG. 7).

Whether inhibition of the active site of multipain and/or the proteasome affected their ability to form a complex was also tested. When the proteasome fraction was preincubated for 10 min with 1 mM DFP, formation of the 1300 kDa structure was still possible, even though this treatment causes a major inhibition of proteasome function (Table VII). By contrast, when multipain was preincubated for 10 min in the presence of cystatin (4 μM), formation of the complex (Table VI) did not occur. Possibly, the cystatin-sensitive proteinase is also essential for complex formation, or cystatin-binding prevents sterically the association reaction.

Effect of Nucleotides

The nucleotide requirement for function of the 1500 kDa complex resembles the nucleotide requirement of multipain (Table VIII, FIG. 7).

As shown in Table VIII, the hydrolysis of Ub-$^{125}$I-lysozyme by the complex was stimulated up to 5-fold by ATP. By contrast, ADP or AMP had no significant effect on this process. No stimulation was seen with the nonmetabolizable ATP analogs, AMP-PNP and ATP-γ-S. Therefore, this reaction seems to require ATP hydrolysis, as has been shown previously for UCDEN. Since the hydrolysis of Ub-conjugates by the complex was linear for at least 2 h in the presence or in the absence of ATP (FIG. 7) and stimulated many-fold with ATP added, this process seems to involve a real enzyme activation by ATP hydrolysis.

TABLE VIII

COMPARISON OF THE EFFECTS OF NUCLEOTIDES ON Ub-LYSOZYME DEGRADATION BY THE COMPLEX OR THE MULTIPAIN

| Compound | Complex | Multipain |
|---|---|---|
| | Relative Activity (%) | |
| None | 100 | 100 |
| ATP | 458 | 743 |
| ADP | 146 | 113 |
| AMP | 99 | 130 |
| AMP-PNP | 109 | 90 |
| ATP-γ-S | 135 | 103 |
| CTP | 410 | 373 |
| GTP | 326 | 435 |
| UTP | 174 | 108 |
| PP$_i$ | 113 | 118 |

Reaction mixtures contained 2 mM of the nucleotide or 10 mM PP$_i$.

As noted in the previous example, ATP enhances the activity of multipain only after a lag-time of 20 min, for reasons that are unknown. It is note-worthy that no such delay was seen with the complex. ATP stimulated its activity against both Ub-lysozyme and lysozyme without any lag-time (FIG. 7).

The requirements for ATP could also be satisfied in part by CTP or GTP, which caused approximately a 3- to 4-fold stimulation of protein breakdown (Table VII). The nucleotide-specificity of the complex resembles prior findings for the nucleotide-specificity for UB-conjugate degradation by reticulocyte extracts, UCDEN and purified multipain (Table VIII). These effects contrast with the activation of the isolated proteasome, which only occurs with ATP and thus probably involves a distinct nucleotide binding protein.

Figure 8:
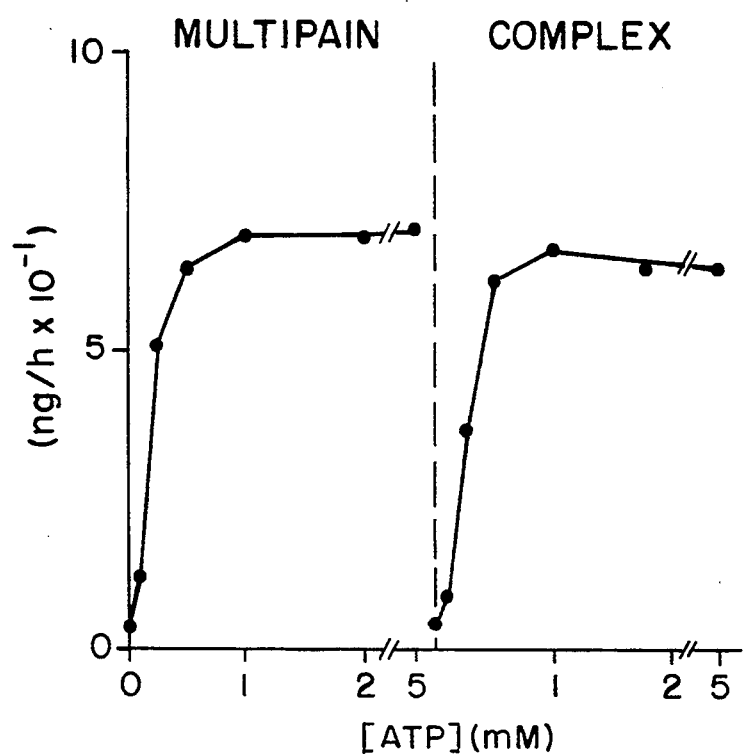
FIG. 8 is a graphic representation of the ATP-dependence for the stimulation of Ub-$^{125}$I-lysozyme degradation by multipain or the complex formed upon incubation of the proteasome and multipain.

When different ATP concentrations were studied, a maximal stimulation of Ub-conjugate degradation was observed by about 0.7 mM. Similar results were observed for both multipain and the 1500 kDa complex (FIG. 8). The data suggest a Km for ATP for both enzymes of 0.3 mM or less, which is far below intracellular ATP concentrations. Thus, the activation of these enzymes by ATP would appear to be physiogiclly relevant. Furthermore, this Km is consistent with earlier observations on the energy requirement for protein breakdown in intact fibroblasts (Gronostajski, R., Pardee, A. B., and Goldberg, A. L., *J. Biol. Chem.*, 260:3344–3349 (1985)), in which nonlysosomal protein breakdown fell only when ATP cellular levels were reduced by more than 70% (i.e., from about 3 mM to below 1 mM).

Although these studies emphasized complex formation as an association between multipain and the proteasome, clearly the complex also contains 4–5 unidentified polypeptides of 65 to 110 kDa and a major band of about 40 kDa, which corresponds to the proteosome inhibitor discussed above. These various bands were present in the partially purified proteasome preparations. Most likely these polypeptides are tightly associated with the proteasome, since they copurified with these particles through ammonium sulfate precipitation and DEAE Mono Q and gel filtration chromatography. However, they do not correspond to the well-defined subunits of 20–30 kDa, many of which have now been cloned and sequenced, and shown to be similar to one another. Fujiwara, T. et al., *Biochemistry*, 28: 7332–7340 (1989). At least some of these larger polypeptides must be essential for complex formation, since more purified proteasome preparations failed to associate with multipain in the presence of ATP.

The nature of these polypeptides and their functions in the larger complex are uncertain. One of the prominent components evident on SDS-PAGE is a 40 kDa polypeptide, which we have shown corresponds to the subunit of the 250 kDa inhibitor of the high molecular weight proteases described by Murakami, et al. Murakami, et al., *Proc. Natl. Acad. Sci.*, 83: 7588–7592 (1986). In addition, evidence obtained in reticuloyctes indicates that this inhibitor corresponds to one of the three components (CF-2) of the 1500 kDa complex. Recently an ATPase which corresponds to one of the proteasome-associated proteins of 95–105 kDa and which may regulate proteasome activity within the complex has been purified. Multipain and the larger complex must contain sites for recognition of Ub-conjugates, for the disassembly of the polyubiquitin chains (an isopeptidase activity), and for cystatin-sensitive proteolytic activity. Thus, in addition to degrading ubiquitinated lysozyme to small peptides, isolated multipain rapidly disassembles multiple ubiquitinated protein, releasing free ubiquitin and protein.

Within the 1500 kDa complex, the proteasome and multipain appear to act synergistically in the breakdown of Ub-conjugated proteins. Both the rate and extent of conjugate degradation were greater with the complex than with equal roles of multipain alone. Moreover, this synergy was only seen when multipain and proteasome were associated with one another. Sequential exposure of the substrates first to multipain and then to the proteasome or mixing the 1500 kDA complexes with the excess proteasomes (Table VI) did not lead to more rapid breakdown of Ub-lysozyme. Since proteasomes by themselves do not digest this substrate, the initial attack must be by multipain, and further digestion of its products must involve the proteasome. It is noteworthy that when the proteasome was added after multipain, it did not digest further the radioactive peptides generated by multipain, as it does in the complex (FIG. 7), where these proteases seem to function in an integrated, perhaps processive, manner. The complex yields short oligopeptides, although in vivo and in reticulocyte extracts, proteins are digested all the way to free amino acids. Presumably other exopeptidases catalyze the completion of this hydrolytic pathway.

Functioning of the complex clearly requires proteolytic activity of each component protease, since it is sensitive to inhibitors of both multipain (cystatin, fatty acids, SDS) and the proteasome (DFP). Although degradation of lysozyme and Ub-lysozyme seem to involve the synergistic functioning of both enzymes, the proteasome-specific activities (peptide or casein degradation) seem unchanged after complex formation. It is of interest that the complex and multipain require similar concentrations of ATP for maximal activity and are both activated also by GTP and CTP. Thus, an ATPase associated with multipain seems to be rate-limiting for activity of the complex, even though additional ATP hydrolytic steps, presumably involving distinct ATPases, are also important in this pathway for complex formatin and for activation of the proteasome. One interesting consequence of complex formation is the disappearance of the long lag-time seen for ATP-activation of multipain. If the lag phase also occurs in vivo, it may mean that if a multipain molecule by itself binds a ubiquitin-conjugate, protein degradation proceeds very slowly until multipain also interacts with a proteasome and forms the larger, more active degradative complex.

EXAMPLE 3

Demonstration of Activation of the Cytosolic ATP-Dependent Proteolytic Pathway in Atrophy of Skeletal Muscle Upon Denervation (Disuse)

As described in Examples 3 and 4, activation of the nonlysosomal (cytosolic) ATP-independent proteolytic pathway has been demonstrated in striated (skeletal) muscle during denervation atrophy and fasting and has been shown to be responsible for most of the increased protein degradation which occurs in both states.

Materials

All materials were obtained from Sigma Chemical Co. (St. Louis, Mo.) unless indicated otherwise. E-64c and leupeptin were gifts from Dr. H. Hanada (Taisho Pharmaceutical Co., Tokyo, Japan).

Muscle Incubations

These experiments used young (60–80 g) male Charles River rats, which were given free access to water and Purina Lab Chow. The soleus muscle was denervated as described previously (Furuno K. et al., *J. Biol. Chem.* 265:8550–8557 (1990)) and sham-operated rats used as controls. At different times after cutting the sciatic nerve or after withdrawal of food, the rats were killed and the soleus or extensor digitorum longus (EDL) muscles were dissected and incubated in vitro, as described previously. Furuno K. et al., *J. Biol. Chem.* 265:8550–8557 (1990); Baracos, V. E.,et al., *Am. J. Physiol.* 251:C588–596 and Kettlehut, I. C. *Am. J. Physiol.*, in press (1991). After a 1 hour preincubation, muscles were transferred to fresh medium, and tyrosine release measured after 2 hours. The $Ca^{2+}$-free Krebs-Ringer bicarbonate buffer used in most experiments contained 5 mM glucose, 0.5 mM cycloheximide, 4 μg/ml insulin, 0.17 mM leucine, 0.1 mM isoleucine, 0.2 mM valine, 10 μM methylamine, and 50 μM E-64. To deplete muscles of ATP, they were incubated with dinitrophenol (at 0.1 and 0.5 mM) and 2 deoxyglucose (5 mM) after removal of glucose from the medium.

To measure overall protein breakdown, the release of tyrosine from cell proteins was followed under conditions where protein synthesis was blocked. The accumulation of 3-methylhistidine was measured to follow the breakdown of myofibrillar proteins; 3-methylhistidine is a specific constituent of actin and myosin Goodman, M. N. *Biochem. J.* 241:121–127 (1987) and Lowell, B. B. et al., *Metabolism*, 35:1121–112. For calculation of proteolytic rates, the net accumulation of tyrosine or 3-methylhistidine in the medium was combined with any changes that occurred in the intracellular pools of these amino acids. Such changes were negligible or small compared to amounts that were released into the medium, as noted previously. Furuno, K. et al., *J. Biol. Chem.*, 256:8550–8557 (1990); Li, J. B., and Goldberg, A. L., *Am. J. Physiol.* 231:441–448 (1976); Baracos, V. E., and Goldberg, A. L., *Am. J. Physiol.*, 251:C588–596 (1986) and Tischler, M. et al., *J. Biol. Chem.*, 257:1613–1621 (1982).

The ATP content of the muscles was determined after preincubation with or without metabolic inhibitors, as described previously. Gronostajski, R. et al., *J. Biol. Chem.*, 260:3344–3349 (1985) and Baracos, V. E., and Goldberg, A. L., *Am. J. Physiol.*, 251:C588–596 (1986).

Results

Measurement of ATP-depletion on Proteolysis in Skeletal Muscle

A simple experimental approach to measuring reliably the ATP-dependent system in intact muscle in vitro has been developed.

Despite the fact that muscle extracts contain the ATP-Ub-dependent system, Matthews, W., et al., *Proc. Natl. Acad. Sci. USA*, 86:2597–2601 (1989) and Fagan, J. M., *Biochem. J.*, 243:335–343 (1987), and ATP-activated protease complexes, Driscoll, J., and Goldberg, A. L., *Proc. Natl. Acad. Sci. USA*, 86:787–791 (1989) and Fagan, J., *J. Biol. Chem.*, 264:17868–17872 (1989), efforts have repeatedly failed to demonstrate a fall in proteolysis upon depleting intact muscles of ATP by using metabolic inhibitors. Goodman, M. N., *Biochem. J.*, 241:121–127 (1987). In other cells studied, including fibroblasts, hepatocytes, reticulocytes, or *Escherichia coli*, Etlinger, J., and Goldberg, A. L., *Proc. Nat. Acad. Sci. USA*, 74:54–58 (1977); Gronostajski, R., et al., *J. Biol. Chem.*, 260:3344–3349 (1985) and Goldbert, A. L., and St. Johh, A., *Ann. Rev. Biochem.*, 45:747–803 (1976), agents that block ATP production were found to reduce protein breakdown by 50–90%. However, when rat leg muscles were incubated in normal media (containing $Ca^{2+}$) with cycloheximide, dinitrophenol (DNP), and 2-deoxyglucose, muscle ATP content decreased by over 90%, yet overall proteolysis increased by 80–200%. Fulks, R., et al., *J. Biol. Chem.*, 250:290–298 (1975). Both the dark soleus and the pale EDL muscles showed a similar activation of proteolysis upon ATP-depletion, as did soleus muscles following denervation or fasting of the animals for 2 days. This rise in proteolysis was seen even when the muscles were incubated under conditions that reduce net protein breakdown (i.e., incubation under tension with insulin and amino acids present). Baracos, V. E., and Goldberg, A. L., *Am. J. Physiol.*, 251:C588–596 (1986). Under these conditions, the muscles developed rigor, as is typical upon ATP-depletion. A variety of evidence (see below) indicated that this anomalous activation of proteolysis was because ATP depletion in muscle leads to $Ca^{2+}$ entry into the cytosol and activation of $Ca^{2+}$ dependent proteases, and that the resulting stimulation of overall proteolysis masks the concomitant inhibition of the ATP-dependent degradative process (Table IX and FIG. 10).

TABLE IX

EFFECT OF INHIBITORS OF DIFFERENT CELL PROTEASES AND ATP PRODUCTION ON BREAKDOWN OF MYOFIBRILLAR AND TOTAL PROTEIN IN DENERVATED SOLEUS

| Pathway Inhibited | Total Proteins Tyrosine Release (pmol/mg/2h) | (%) | Myofibrillar Proteins 3-Methylhistidine Release (pmol/mg/2h) | (%) |
|---|---|---|---|---|
| None | 328 ± 10 | 100 | 5.11 ± 0.21 | 100 |
| Lysosomal | 330 ± 11 | 100 | 5.05 ± 0.19 | 99 |
| +$Ca^{2+}$ Dependent + Lysosomal | 324 ± 10 | 99 | 5.23 ± 0.22 | 100 |
| ATP-Dependent Pathway +$Ca^{2+}$ Dependent + Lysosomal | 112 ± 14* | 34 | 2.24 ± 0.17* | 44 |

Values are the means±SEM for 5 muscles three days after section of the sciatic nerve. Significant difference, *p<0.01. Protein breakdown measured in muscles at resting length in $Ca^{2+}$-free Krebs-Ringer bicarbonate buffer containing insulin and amino acids. Methylamine (10 μM) is an inhibitor of lysosomal proteolysis E-64c (50 μM) inhibits both lysosomal thiol protease and the calpain, dinitrophenol (0.1 mM), and 2-deoxyglucose (2 DG) (5 mM) were added to inhibit the ATP-dependent pathway. Glucose was omitted from media containing DNP and 2-deoxyglucose.

Conditions for Measuring ATP-dependent Proteolysis in Incubated Muscles

It was possible to establish incubation conditions for measuring selectively the ATP-dependent and energy-independent nonlysosomal degradative processes. In order to measure the ATP-dependent process, it was necessary to prevent the activation of $Ca^{2+}$-dependent proteases upon ATP-depletion (see above). The muscles were therefore maintained at resting length (Baracos, V. E., and Goldberg, A. L., Am. J. Physiol., 251:C588–596 (1986)), in $Ca^{2+}$-free media containing E-64c, a potent inhibitor of the calpains. Hanada, K. et al., Agric. Biol. Chem., 42:523–528 (1978). Prior studies showed that these conditions block the activation of proteolysis in anoxic (shortened) muscles (Baracos, V. E. and A. L. Goldberg, Am. J. Physiol., 251:C588–596 (1986); and Kettlehut, I. C. et al., Am. J. Physiol. (1991) in press) or upon treatment with $Ca^{2+}$ ionophores (Zeman, R. J. et al., J. Biol. Chem. 260:13619–13624 (1985); Baracos, V. E. and A. L. Goldberg, Am. J. Physiol., 251:C588–596 (1986); and Baracos, V. E. et al., Am. J. Physiol., 13:E702–710 (1986)). As described previously, in this medium inhibitors of ATP production were found to reduce protein breakdown in muscle (FIG. 9), as they do in other cells. Gronostajski, R., et al., J. Biol. Chem., 260:3344–3349 (1985) and Goldberg, A. L., and St. John, A., Ann. Rev. Biochem., 45:747–803 (1976). To prevent lysosomal protein breakdown in these muscles (Furuno K., and Goldberg, A. L., Biochem. J., 237:859–864 (1986); Zeman, R. J. et al., J. Biol. Chem., 260:13619–13624 (1985) and Furuno K., et al., J. Biol. Chem., 265:8550–8557 (1990)), the incubation medium also contained insulin and amino acids, which suppress autophagy (Dicem J. F., FASEB J., 1:349–356 (1987) and Lardeux, B. R., and Mortimore, G. F., J. Biol. Chem., 262:14514–14519 (1987)) and methylamine, an inhibitor of lysosomal acidification. Poole, B., and Okhuma, S. J. Cell. Biol., 90:665–669 (1981). In addition, the E-64c inactivates lysosomal thiol proteases (cathepsins B,H, and L) in intact muscles, Baracos, V. E., et al., Am. J. Physiol., 13:E702–710 (1986). These incubation conditions do not affect the levels of ATP or creatine phosphate in the tissues or the rates of protein synthesis. Baracos, V. E., et al., Am. J. Physiol. 251:C588–596 and Kettlehut, I. C. Am. J. Physiol., in press (1991).

Figure 9A:
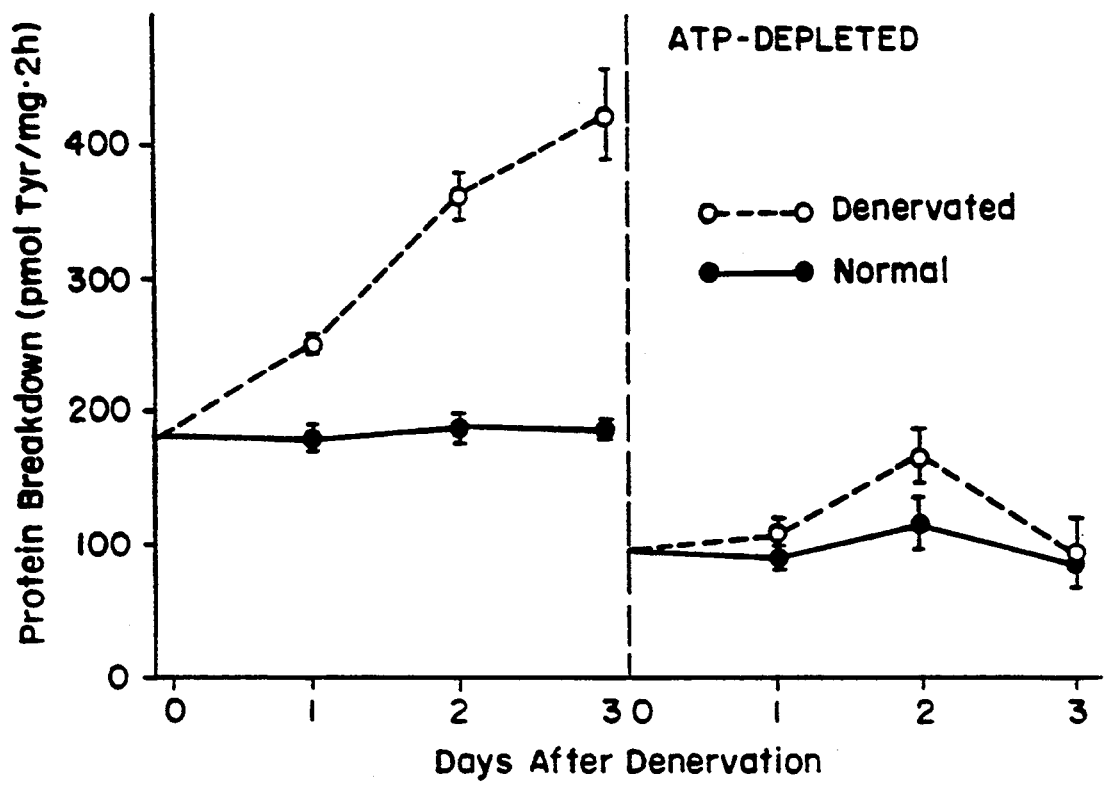
FIG. 9 is a graphic representation of the effect of ATP-depletion on protein breakdown in denervated and normal soleus muscles. These data show that overall proteolysis increases primarily by activation of the ATP-dependent pathway following denervation. Values are the means±the SEM for at least 5 rats in which both sciatic nerves were cut, or for unoperated normal rats. Upper Left: Total protein degradation on each day after cutting the sciatic nerve and in normal muscles from rats of similar size (60–70 g), Upper Right: Effect of ATP-depletion on rates of proteolysis. Lower Left: The relative changes in total protein breakdown and in the energy-independent proteolytic process after denervation (i.e., the difference in means rates of proteolysis between denervated muscles and normal ones). Lower Right: The relative changes in the ATP-dependent process after denervation.
Figure 9B:
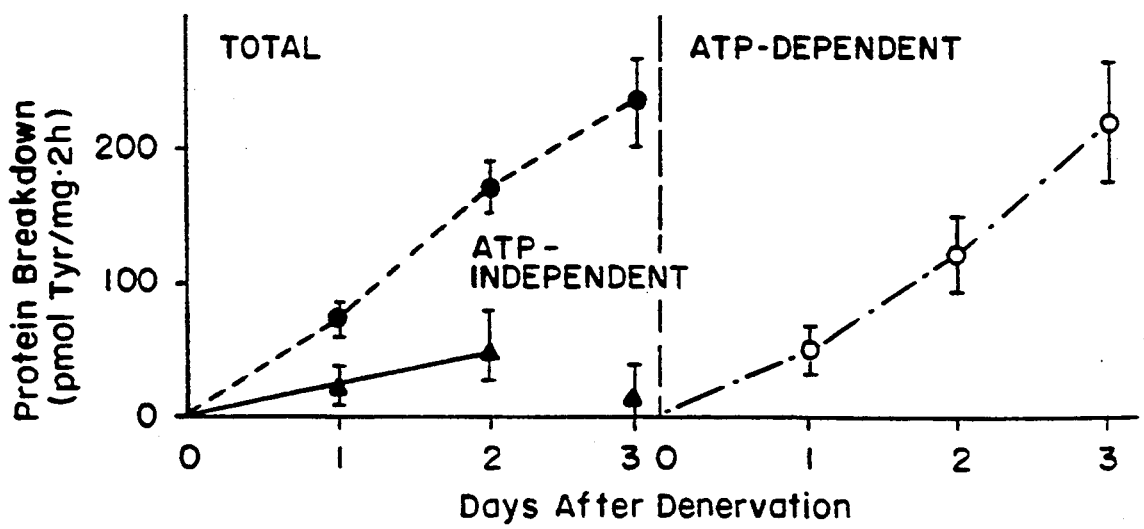
Figure 10:
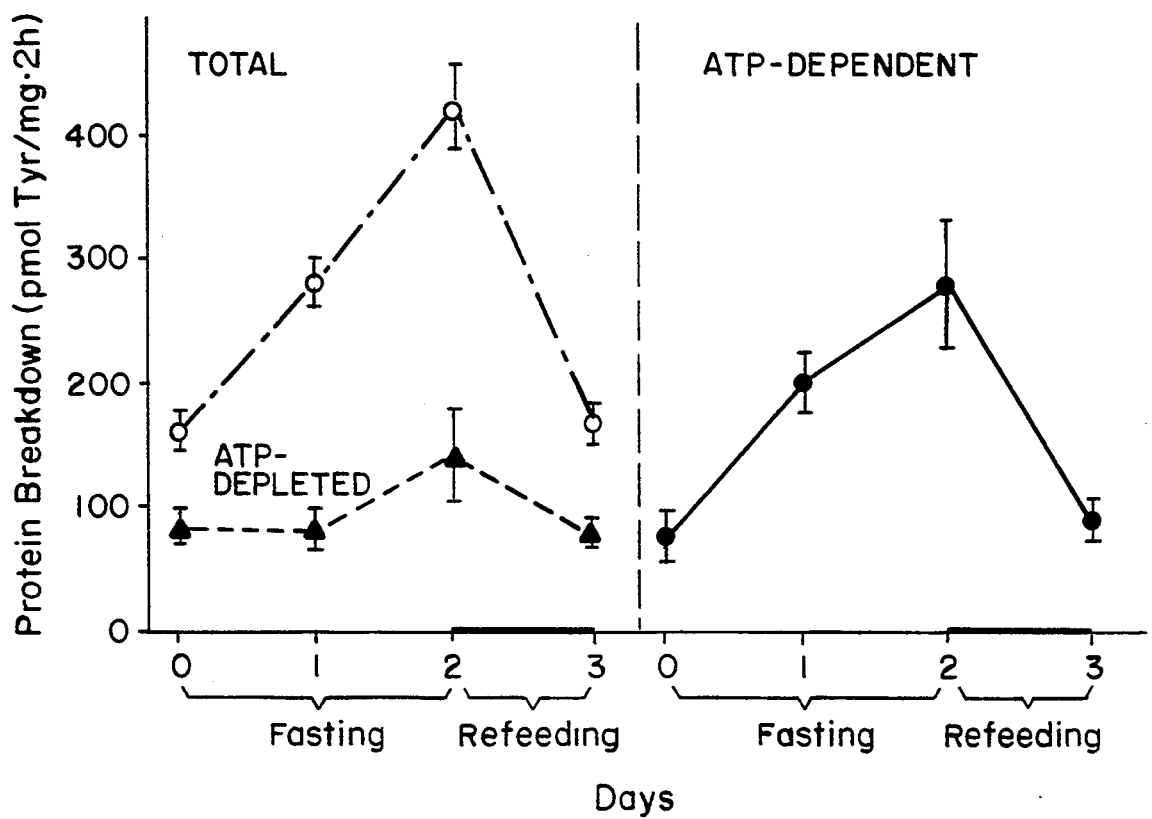
FIG. 10 is a graphic representation of the effects of fasting and refeeding on protein breakdown in rat extensor digitorum longus muscle. Left panel: Total protein breakdown and the energy independent process in muscles from fed or fasted rats were measured at different times after removal of food and 24 hours after refeeding. Right panel: The ATP-independent component of protein breakdown. Values are the means±the SEM for 6 rats.

Even though lysosomal and $Ca^{2+}$-dependent proteolytic systems were blocked, the muscles showed linear rates of protein breakdown (FIG. 10). These rates were similar to those in muscles maintained in complete medium lacking the inhibitors. Baracos, V. E., et al., Am. J. Physiol. 251:C588–596 (1986); Kettlehut, I. C. Am. J. Physiol., in press (1991) and Baracos, V. E., et al., Am. J. Physiol., 13:E702–710 (1986). This finding agrees with prior studies showing that lysosomal and $Ca^{2+}$-dependent processes make a very minor contribution to "basal" protein breakdown. Rechsteiner, M., Ann. Rev. Cell Biol., 3:1–30 (1987); Dice, J. G., FASEB J., 1:349–356 (1987); Gronostajski, R., et al., J. Cell. Physiol., 121:189–198 (1984); Furuno K., and Goldberg, A. L., Biochem. J., 237:859–864 (1986); Zeman, R. J., et al., J. Biol. Chem., 260:13619–13624 (1985) and Baracos, V. E., and Goldberg, A. L., Am. J. Physiol., 251:C588–596 (1986). When normal soleus or EDL muscles in this medium were depleted of up to 96% of their ATP (with dinitrophenol and 2-deoxyglucose), there was a 50–70% reduction in protein degradation (FIG. 10), which resembles the fraction of protein breakdown that is ATP-dependent in fibroblasts. Gronostajski, R., et al., J. Biol. Chem., 260:3344–3349 (1985). To quantitate this ATP-dependent component, the muscle of one limb was depleted of ATP, while the contralateral muscle served as a control. The rate of protein degradation in the two limbs were compared. The net decrease in overall protein breakdown comprises the ATP-dependent component and could thus be measured highly reproducibly in muscles in different physiological states (FIGS. 9 and 10). Kettlehut, I. C., et al., Diabetes/Metabolism Reviews, 4:751–772 (1988); Han, H. Q., et al., Federation Proc., 2:A564 (1988) and Kettlehut, I. C., et al., Federation Proc., 2:A564 (1988).

To deplete muscles of ATP, they were preincubated for 1 hour with 2,4-dinitrophenol (DNP) and 2-deoxyglucose to block both oxidative phosphorylation and glycolysis. In fibroblasts (Gronostajski, R., et al., J. Biol. Chem., 260:3344–3349 (1985)), and hepatocytes, Hershko, A., and Tomkins, G. M., J. Biol. Chem., 246:710–714 (1971), these agents block ATP production and protein breakdown reversibly. Neither inhibitor affected the ATP-dependent or energy-independent proteolytic systems in cell-free extracts of muscle. Typically, preincubation with DNP (0.1mM) and 2-deoxyglucose (5 mM) for 1 hour reduced ATP content by >85%, and 0.5 mM DNP with deoxyglucose (5 mM) depleted ATP by >96% in normal muscles. These treatments caused similar reductions in ATP content in denervated muscles and in muscles from fasted animals whose initial ATP stores were also similar to those of control muscles. These different concentrations of DNP caused a similar reduction in protein breakdown. In these ATP-depleted tissues, the residual (energy-independent) protein degradation occurred at linear rates for several hours, and the intracellular pools of tyrosine were similar to those in the contralateral (untreated) muscles.

Changes in Protein Breakdown during Denervation Atrophy

When the sciatic nerve of a rat is cut, the unused soleus muscle on that limb undergoes rapid atrophy, losing about 30% of its weight and protein content within 3 days. Furuno K., et al., *J. Biol. Chem.*, 265:8550–8557 (1990) and Goldspink, D. F., *Biochem. J.*, 156:71–80 (1976). During this period, overall protein breakdown increases and by 3 days is 2- to 3-fold greater than in the contralateral control soleus, Furuno K., et al., *J. Biol. Chem.*, 265:8550–8557 (1990). A similar rise in overall proteolysis was seen when the denervated and control muscles were incubated in normal Krebs-Ringer bicarbonate or under conditions which prevent lysosomal or $Ca^{2+}$-dependent proteolysis, Furuno K., et al., *J. Biol. Chem.*, 265:8550–8557 (1990).

To test whether the ATP-dependent pathway is responsible for the enhanced protein breakdown, the atrophying and control soleus were depleted of ATP at different times after nerve section, as described above. Control experiments showed that neither denervation for 3 days nor fasting affected the muscle's initial ATP content or the decrease in ATP induced with DNP and deoxyglucose (Table IX). However, depletion of cellular ATP caused a much larger net decrease in proteolysis in the denervated muscles than in controls (FIG. 9). For example, in a typical experiment these inhibitors decreased proteolysis by $53 \pm 6$ pmol/mg/2 h (43%) in control soleus and by $146 \pm 13$ pmol/mg/2 h (64%) in soleus denervated for 3 days (p<0.01). After depletion of ATP, the residual rates of proteolysis in the denervated and control tissues did not differ (FIG. 9). Thus, in the atrophying muscles, a nonlysosomal ATP-dependent proteolytic process seems to be activated, while no change occurs in the residual energy-independent process.

Overall protein breakdown in the soleus was enhanced by 1 day after nerve section and then rose progressively during the next 3 days (FIG. 9). The ATP-dependent component increased in parallel with overall proteolysis over this time period. In contrast, the energy-independent process remained constant throughout. Thus, the energy-independent process must represent a distinct process and is not just an artifact due to a failure to block completely the ATP-dependent pathway. The rise in the ATP-requiring process could account for all of the increased protein breakdown in the denervated muscle maintained in this way (FIG. 9).

EXAMPLE 4

Demonstration of Activation of the Cytosolic ATP-Dependent Proteolytic Pathway in Atrophy of Skeletal Muscles in Fasting Effects of Fasting and Refeeding Muscles of fasting rats were studied to test whether this degradative process is activated under other physiological conditions where muscle protein breakdown rises. In animals deprived of food, there is a rapid increase in muscle protein breakdown which appears essential to provide the organism with amino acids for gluconeogenesis. Li, J. B., and Goldberg, A. L., *Am J. Physiol.*, 231:441–448 (1976); Lowell, B. B., et al., *Biochem. J.*, 234:237–240 (1986); Goldberg, A. L., et al., *Federation Proc.*, 39:31–36 (1980) and Lowell, B. B., et al., *Metabolism*, 35:1121–112 (1986). When the EDL muscles from fasted animals were incubated under conditions that block lysosomal and $Ca^{2+}$-dependent degradative processes, they showed a large increase in overall proteolysis (FIG. 10), in accord with observations on 3-methyl-histidine production, Lowell, B. B., et al., *Metabolism*, 35:1121–112 (1986). However, when the muscles from the fasted or fed animals were incubated with metabolic inhibitors to prevent the ATP-requiring process, these differences in their rates of protein breakdown were eliminated. Thus, the increase in muscle proteolysis in fasting seems to be due to an enhancement of an energy-requiring nonlysosomal process.

Figure 12:
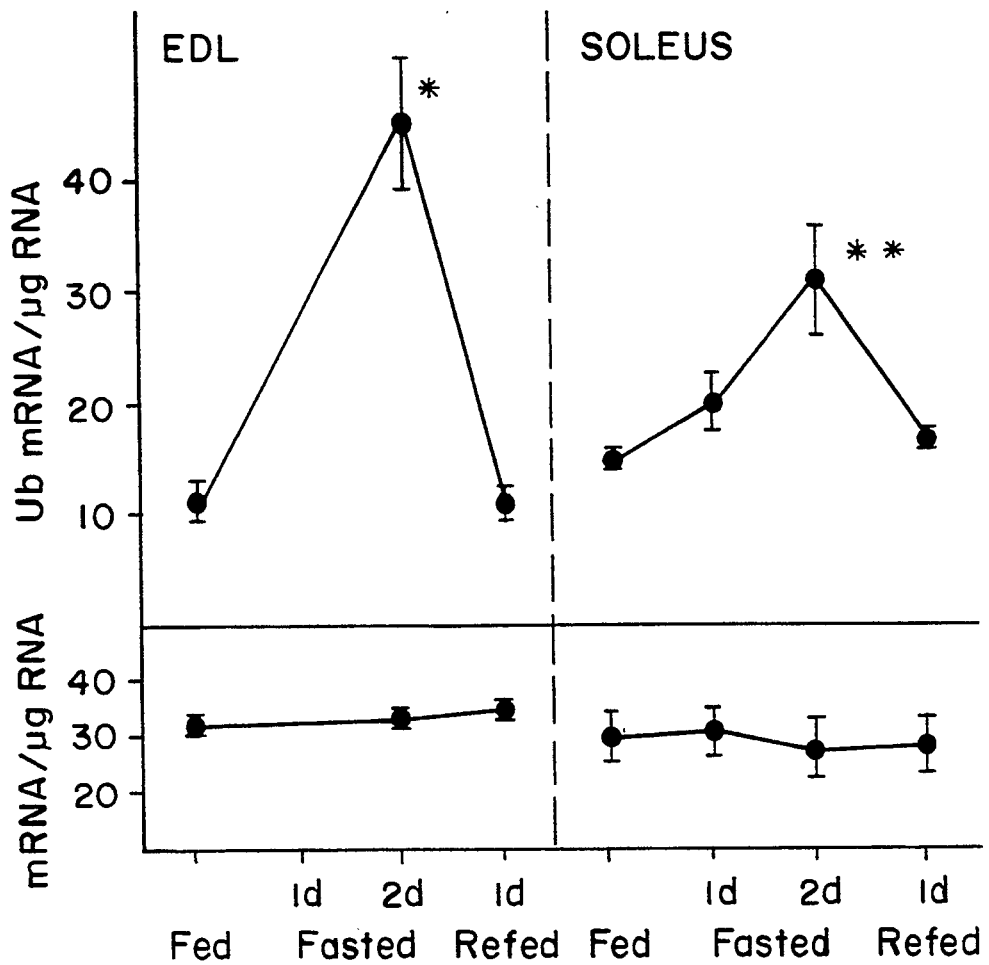
FIG. 12 is a graphic representation of levels of total mRNA determined by dot blot analysis in soleus muscles of fasted and fasted-refed rats, as described in Example 6. Significant difference from fed animals, $*p < 0.005$, $**p < 0.05$.

The rise in this ATP-requiring process was evident 1 day after removal of food and could account for all of the increased proteolysis seen in the EDL muscle under these incubation conditions (FIG. 12). In fasting, the enhancement of overall proteolysis is greater in the pale muscles, such as the EDL, than in the dark soleus. Li, J. B., and Goldberg, A. L., *Am. J. Physiol.*, 231:441–448 (1976). Accordingly, the soleus muscle showed a similar, but a smaller, rise in the ATP-dependent process. On the average, the rise in proteolysis in the soleus in fasting was 20–48% smaller than in the pale EDL (p<0.01).

Upon refeeding the rats, protein breakdown in the EDL decreased back to basal levels within 1 day (FIG. 10). Again, this response was due to a change in the ATP-dependent process with no alteration in the energy-independent pathway.

One of the major features of denervation atrophy is differential loss of myofibrillar proteins, but the system responsible for their accelerated degradation has not been identified. Furuno K., et al., *J. Biol. Chem.*, 265:8550–8557 (1990). The breakdown of these proteins can be followed by measuring 3-methyl-histidine production, which is a specific constituent of actin, and in certain muscles of myosin. Goodman, M. N., *Biochem. J*, 241:121–127 (1987) and Lowell, B. B., et al., *Metabolism*, 35:1121–112 (1986). When these proteins are hydrolyzed, this amino acid cannot be reutilized in protein synthesis, and thus its appearance as an indication of myofibrillar protein breakdown. Goodman, M. N., *Biochem. J*, 241:121–127 (1987) and Lowell, B. B., et al., *Metabolism*, 35:1121–112 (1986). The increased production of 3-methyl-histidine after denervation is markedly inhibited by blocking ATP production, but is not affected by treatments that prevent lysosomal and $Ca^{2+}$-dependent proteolysis. Furuno K., et al., *J. Biol. Chem.*, 265:8550–8557 (1990). These findings and those for overall protein breakdown (FIG. 11) indicate that enhancement of a nonlysosomal ATP-dependent process is primarily responsible for the muscle atrophy.

EXAMPLE 5

Studies in Cell-Free Extracts to Assess Activation of the ATP-ub-Dependent System Measurement of Proteolysis in Muscle Extracts Psoas muscles from fed and fasted rabbits were used to obtain sufficient material for assay of the ATP-dependent system in cell-free extracts. Fasted rabbits were deprived of food for sufficient time to cause a weight loss of about 20% (similar to that seen in rats deprived of food for 1 day). The animals were anesthesized, and their psoas muscles dissected and homogenized as described previously. Fagan, J. M., et al., *J. Biol. Chem.*, 261:5705–5713 (1986).

After centrifugation at $10,000 \times g$ and then at $100,000 \times g$, the muscle extracts were fractionated on DE52 cellulose to remove ubiquitin and most cell proteins, as described previously. Han, H.Q. et al., *Federation*

Proc, 2:A564 (1988) and Waxman, L., et al., *J. Biol. Chem.*, 262:2451–2457 (1987). The fraction containing the ATP-ubiquitin-dependent proteolytic system (Herskho, A., *J. Biol. Chem.*, 263:15237–15240 (1988); Rechsteiner, M., *Ann. Rev. Cell Biol.*, 3:1–30 (1987) and Fagan, J. M., et al., Biochem J., 243:335–343 (1987)) was eluted with 0.5M NaCl ("Fraction II"), dialyzed against a buffer containing Tris (50 mM, pH7.8), dithiothreitol (1 mM), and 20% glycerol, and concentrated before assay of activity. Degradation of endogenous muscle proteins was assayed by measuring the production of free tyrosine, which was determined fluorometrically after precipitation of proteins with trichloroacetic acid. Tischler, M. et al., *J. Biol. Chem.*, 257:1613–1621 (1982) and Fulks, R., et al., *J. Biol. Chem.*, 250:290–298 (1975). In addition, the degradation of $^{14}$C-casein was assayed by measuring the production of acid-soluble radioactivity. Waxman, L., et al., *J. Biol. Chem.*, 262:2451–2457 (1987) and Fagan, J. M., *Biochem J.*, 243:335–343 (1987).

These findings from Examples 3 and 4 strongly suggested that the soluble ATP-requiring proteolytic system which involves ubiquitin is activated during fasting or denervation atrophy. However, such measurements on intact muscles cannot distinguish other possible changes in these catabolic states. Therefore, soluble cell-free extracts of muscles from fed and fasted rabbits were used in order to test whether the increased proteolysis in fasting is due to activation of the ATP-Ub-dependent system. Cell-free preparations showing ATP-Ub-dependent proteolysis have been described in extracts of rabbit muscles. Fagan, J. M., et al., *Biochem. J.*, 243:335–343 (1987). The proteolytic system from rabbit muscles were partially purified by high-speed centrifugation and ultracentrifugation to remove myofibrils and membranous components, and then it was subjected to DEAE chromatography to remove most (>90%) of the soluble proteins, including free ubiquitin. The resulting fraction contains all the enzymes for Ub-conjugation and hydrolysis of Ub-protein conjugates, Herskho, A., *J. Biol. Chem.*, 263: 15237–15240 (1988); Rechsteiner, M., *Ann. Rev. Cell Biol.*, 3:1–30 (1987); Waxman, L., et al., *J. Biol. Chem.*, 262:2451–2457 (1987); Fagan, J. M. et al., *Biochem. J.*, 243:33–343 (1987) and Hough, R., et al., *J. Biol. Chem.*, 261:2400–2415 (1986), as well as the ATP-activated form of the proteasome (multicatalytic proteolytic complex), Waxman, L., et al., *J. Biol. Chem.*, 262:2451–2457 (1987).

In these extracts, the hydrolysis of endogenous proteins (shown by tyrosine production) increased 5-to 9-fold upon addition of ATP and even further upon addition of ATP with ubiquitin (Table X). This ATP-activated process was 2-fold greater in extracts from fasted animals than from control animals. The addition of ubiquitin further enhanced proteolysis in both preparations, but it seemed to reduce the relative increase seen in fasting. In addition, the small amount of proteolysis seen in the absence of added ATP was also greater in the extracts from fasted animals.

TABLE X

EFFECTS OF FASTING OF RABBITS ON ATP-UBIQUITIN-ACTIVATED PROTEOLYSIS IN EXTRACTS OF PSOAS MUSCLE

| Condition | Hydrolysis of Endogenous Proteins | | |
|---|---|---|---|
| | No addition | +ATP | +ATP + Ub |

TABLE X-continued

EFFECTS OF FASTING OF RABBITS ON ATP-UBIQUITIN-ACTIVATED PROTEOLYSIS IN EXTRACTS OF PSOAS MUSCLE

| | (nmol try released/2 hr) | | |
|---|---|---|---|
| Fed | 0.6 ± 0.1 | 5.7 ± 0.9 | 9.2 ± 1.8 |
| Fasted | 2.0 ± 0.1 | 10.8 ± 2.1 | 15.2 ± 3.7 |
| Increase | 1.4 ± 0.1* | 5.1 ± 2.3* | 6.0 ± 3.8 |
| % Change | 234% | 90% | 65% |
| | $^{14}$C-Casein Hydrolysis (ug casein hydrolyzed/1 hr) | | |
| Fed | 1.1 ± 0.2 | 1.5 ± 0.2 | 1.6 ± 0.2 |
| Fasted | 1.6 ± 0.2 | 2.3 ± 0.2 | 2.5 ± 0.2 |
| Increase | 0.5 ± 0.3 | 0.8 ± 0.3 | 0.9 ± 0.3** |
| % Change | 46% | 56% | 53% |

Values are the means ± SEM for 7 rabbits. Significant difference, *p < 0.05 and **p < 0.01. These assays were performed on partially purified proteolytic fractions ("Fractions II") as further described in the Example. Breakdown of endogenous proteins (tyrosine production) was measured for 2 hours at 37° C. with 5 mg of Fraction II protein. Degradation of $^{14}$C-Casein was assayed at 37° C. for 1 hour with 400 μg of Fraction II protein and 20 μg $^{14}$C-casein. Assays were performed in Tris (50 mM, pH 7.8), dithiothreitol (1 mM), and MgCl (10 mM) in a final volume of 200 μM ATP (5 mM) or ubiquitin (15 μM) were added where indicated.

To further test for an activation of the ATP-dependent degradative system, rather than an alteration in the endogenous cell proteins which served as substrates, $^{14}$C-methyl-casein was used as a substrate (Table X). This protein is also degraded rapidly by ATP-independent enzymes, and this ATP-independent process appeared to increase upon fasting (although this trend did not reach statistical significance). Addition of ATP or ATP and Ub caused a clear increase in casein degradation, and this ATP-dependent casein hydrolysis, whether or not Ub was also present, was almost 2-fold greater after food deprivation of the rabbit for 6 days. Detailed time-courses could not be pursued because of the difficulties in such preparations and the tendency of the rabbits to store large amounts of food in their gastrointestinal tract. However, no such increase in proteolysis was seen in extracts of muscles from rabbits deprived of food for shorter periods than 6 days, at which time they showed no weight loss and still retained appreciable food in the intestines. In any case, the studies with exogenous or endogenous substrates clearly indicate an increased capacity of the ATP-dependent degradative system in fasting, as suggested by the measurements on incubated muscles (FIG. 10).

EXAMPLE 6

Further Evidence for Activation of the ATP-Ubiquitin-Dependent Process in Various Catabolic States Activation of the ATP-ubiquitin-dependent proteolytic process was shown to be responsible for most of the increased protein degradation in skeletal muscle during denervation atrophy, fasting and febrile infection, as described below. In addition, levels of polyubiquitin mRNA and mRNA for proteosome units are shown to increase in skeletal muscle during denervation atrophy, fasting and febrile infection, as shown below. Similar data have been obtained in rats with metabolic acidosis (induced by injection with ammonium chloride) or suffering with cancer cachexia (induced by a transplantable hepatoma growing in ascites).

Materials and Methods

Muscle preparations

Young male rates (60–80 g, Charles River CD strain) were maintained on Purina Lab chow and water "ad libitum". All treatments were carried out as described in Example 3. To denervate the soleus muscles of one hind limb, the sciatic nerve was cut about 1 cm above the popliteal fossa, while the animals were under ether anesthesia. Furuno, K. et al., *J. Biol. Chem.*, 265: 8550–8552 (1990). In all cases the animals were killed by cervical dislocation and the EDL and soleus muscles were dissected as described in the previous examples.

RNA preparation and Northern analysis

Total RNA from muscle was isolated by the guanidinium isothiocyanate/CsCl method, and electrophoresis of RNA was performed in 1% agarose gels containing 0.2M formaldehyde. Maniatis, T. et al., *Molecular Cloning: A Laboratory Manual*, Cold Spring Harbor Laboratory, N.Y. (1982). The RNA was transferred from the gel to nylon membrane (Gene Screen Dupont, NEN Research Pro.) in 20 X SSC (3M sodium chloride/0.3M sodium citrate). RNA was crosslinked to the membrane by UV light at 1200 microjoules on a Stratalinker apparatus (Strategene Co., CA). Membranes were hybridized at 65° C. with 32P-labeled cDNA probes prepared by the random-primer method. Feinherg, A. P. and B. Vogelstein, *Anal. Biochem.*, 132: 6–13 (1983). The hybridization buffer contained polyvinylpyrolidone-40,000 (0.2%), Ficoll-400,000 (0.2%), bovine-serum albumin (BSA, 0.2%), Tris-HCl (0.05M, pH 7.5), NaCl (1M), sodium pyrophospate (0.1%), sodium dodecyl sulfate (SDS, 1%) and salmon sperm DNA (100 μg/ml). After hybridization, the filters were washed in 0.5 X SSC/1% SDS at 42° C. or 65° C. Membranes were exposed to XAR-2 film (Kodak) for autoradiography.

For dot blot analysis, four different concentrations (2-fold dilutions from 1.5 μg) of total denatured RNA from the soleus or EDL muscles were spotted on Gene Screen membranes. The amount of RNA applied to each dot was maintained at 1.5 μg by adding *E. coli* tRNA (which in the absence or rat muscle RNA did not show any hybridization). The hybridization probes were a Ub cDNA fragment (Agell, N. et al., *Proc. Natl. Acad. Sci. USA*, 85:3693-3697 (1988), other HSP cDNA probes and oligo dT (Harley, C.B., *Gene Anal. Tech.*, 4:17–22 (1997) to measure total polyA-containing RNA. Ub cDNA was kindly provided by Dr. M. Schlesinger (Washington University Medical School), the HSP70 cDNA by Dr. R. Voellmy and the HSP 90 cDNA by Dr. L. A. Weber (University of Miami School of Medicine). Blots were hybridized with the Ub probe at 65° C. and with oligo-dT at room temperature and washed at these same temperatures. Levels of polyUb RNA and total mRNA were determined from the dot intensities of the autoradiograms by automated densitometric scanning. The unpaired Student's t-test was used in statistical analyses to compare muscle of fed and fasted animals and the paired t-west was used to compare contralateral denervated and control muscles.

Measurements of total ubiquitin content (which includes both free Ub and Ub ligated to proteins) were carried out using the immunochemical method described by Riley D. A. et al., *J. Histochem. Cytochem.*, 36:621–632 (1988).

Results

Ubiquitin mRNA in Fasting

Figure 11:
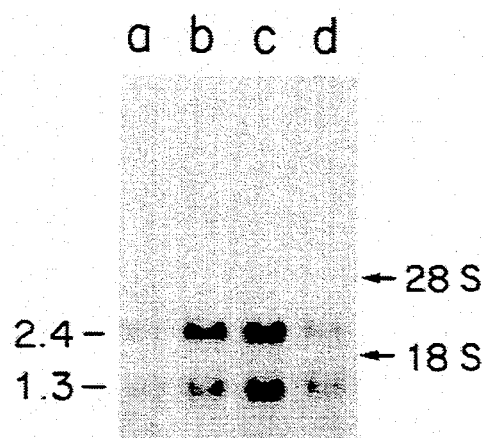
FIG. 11 shows results of Northern blot analysis Ub mRNA in muscle from fasting and fasted-refed rats. Shown are levels of polyUb mRNA in 10 μg of total RNA/lane isolated from soleus muscle of fed rats (a) and fasted rats for 24 hrs. (b) 48 hrs. (c) or fasted 48 hrs. and refed for 24 hrs. (d) 28S and 18S indicate the positions of these ribosomal RNAs.

To test whether the level of Ub mRNA increases when muscle protein breakdown rises, the levels of polyUb transcripts in rat muscles were determined at different times after food deprivation. As shown in FIG. 11, the soleus contained two transcripts of 2.4 and 1.3 Kb, which correspond to the sizes of polyUb genes in other species (Schlesinger, M. J. and Bond, U. in *Oxford Surveys on Eukaryotic Genes* (Maclean, N., ed.) 4:76–91 (1987)). The levels of both transcripts increased progressively in the muscles of fasted animals. The relative levels of Ub mRNA in these tissues of fasting rats were measured by dot-blot analysis and autoradiography (FIG. 12). After 48 hours of food deprivation, the levels of total Ub mRNA in the extensor digitorum longus (EDL) muscle showed a 4-fold increase over muscles of control animals (FIG. 13, upper panel). The soleus muscle, which atrophies less than the EDL in fasting (Li, J. B. and Goldberg, A. L., *Am. J. Physiol,* 231:441–448 (1976)), showed a 2-fold increase in Ub mRNA. A third minor Ub transcript of 0.9 Kb could also be detected by overexposing the autoradiograms. It corresponds in size to the product of the Ub-extension gene (Schlesinger, M. J. and Bond, U. in *Oxford Surveys on Eukaryotic Genes* (Maclean, N., ed.) 4:76–91 (1987)) whose expression is associated with biogenesis of ribosome (Finley, D. et al., *Nature*, 338:394–401 (1989); Redman, K. and Rechsteiner, M, *Nature*, 338:438–440 (1989)). This transcript did not increase with fasting, unlike polyUb mRNA which thus appears to increase selectively.

To examine whether the increase in polyUb mRNA was reversible, some of the fasted rats were then provided food for 24 hours. By 24 hours of refeeding, the levels of polyUb mRNA in these muscles had returned to levels in muscles of normal animals. This rise and fall in the amount of polyUb mRNA thus parallels the changes in overall rates of protein degradation (FIG. 10) and in the ATP-dependent degradative process (FIG. 10).

To determine if polyUb mRNA is regulated in a specific manner in fasting, whether the total amount of RNA or of mRNA in these muscles may also have changed after food deprivation in a similar way as polyUB mRNA was assessed. The total RNA content was measured by absorbance spectrophotometry and the total amount of poly-A-containing RNA on the dot blots was measured using a $^{32}$P-oligo dT probe. In contrast to polyUb mRNA, the total RNA content and the amount of mRNA (i.e., poly-A-containing RNA) in the soleus and EDL decreased to approximately 50% of the levels found in muscles of fed animals. Total RNA fell from $72 \pm 3.5$ to $35 \pm 1.6$ ug/muscle and total mRNA (expressed in arbitrary densitometric units) from $2133 \pm 376$ to $1004 \pm 20$ units/muscle in the soleus during fasting. In the fasted EDL, total RNA decreased from $68 \pm 6$ to $38.5 \pm 1$ ug/muscle and total mRNA from $710 \pm 73$ to $413 \pm 11$ units/muscle. The ratio of total mRNA to total RNA, unlike Ub mRNA, thus, did not change significantly during the 48 hours of food deprivation or during refeeding (FIG. 12).

Ub mRNA in Other Tissues

Subsequent experiments tested whether the increase in polyUb mRNA in fasting is unique to skeletal muscle or whether other rat tissues show similar responses 2 days after food deprivation. Enhanced proteolysis in fasting has been attributed primarily to activation of a lysosomal process. In the heart (ventricle) of fasting rats, a rise in polyUb mRNA occurred similar to that seen in EDL muscle. By contrast, no such change was seen in any other tissue tested, including liver, spleen, adipose tissue, brain, testes and kidney. In the liver, kidney, and adipose tissue a marked loss of weight and protein occurred on fasting, but as expected neither testes nor brain showed significant weight loss under these conditions. Thus, during fasting, the rise in Ub mRNA appears to be a specific adaptation in striated muscle and is not seen in other tissues.

Ubiquitin mRNA Levels In Denervation Atrophy

A similar 2- to 3-fold acceleration of the ATP-dependent proteolytic process occurs in muscle during denervation atrophy. To test whether in this condition the expression of polyUb genes may also be activated, we analyzed the levels of Ub mRNAs from the soleus at 1 and 3 days after denervation (Table XI). At 1 and 3 days following denervation, the levels of polyUb transcripts increased markedly above the levels in the contralateral control muscle. Dot blot analysis of the muscles revealed a 2 to 3-fold increase in polyUb mRNA content as a proporation of total mRNA following denervation (Table XI). Although the size of Ub mRNA level of control muscles did not change during the course of this study, by contrast the total RNA in the denervated soleus decreased by 40% in 3 days (Table XI).

This increase in mRNA for ubiquitin correlated with accelerated proteolysis in the muscle.

TABLE XI

EFFECT OF UNILATERAL DENERVATION OF RAT SOLEUS MUSCLE ON THE CONTENT OF PolyUb mRNA, TOTAL RNA AND WEIGHT

| Time after operation | Control | Denervated | Control | Denervated |
|---|---|---|---|---|
| Ub mRNA/μg total RNA | 2.4 ± 0.2 | 6.1 ± 0.6* | 2.5 ± 0.2 | 5.4 ± 0.9** |
| mRNA/μg total RNA | 23.8 ± 1.4 | 23.1 ± 1.4 | 22.7 ± 0.8 | 23.7 ± 1.4 |
| Total RNA (μg)/soleus | 42.3 ± 2.2 | 36.7 ± 1.3** | 54.0 ± 6.5 | 32.5 ± 4.2* |
| Muscle weight (mg) | 28.8 ± 0.7 | 26.3 ± 0.8** | 30.7 ± 1.1 | 23.5 ± 2.1* |
| Weight loss (% of control) | | −9%** | | −23%* |

Values represent the mean ± S.E.M. for 6 animals. Significance difference from control value, *$p < 0.005$, **$p < 0.05$.

Ubiquitin content of the muscles

To determine whether the increase in polyUb mRNA actually resulted in increased production of Ub, the total amount of this protein in the muscles was quantitated by immunoassay (Table XII). These arrays measured both free Ub and Ub conjugated to cell proteins. (Riley, D. A. et al., *J. Histochem. Cytochem.*, 36:621-632 (1988) In EDL muscles from animals fasted 2 days, a 63% increase in Ub levels was observed over levels in fed controls. An even larger increase of 91% was seen in the Ub content of soleus muscles 2 days after cutting the sciatic nerve. Thus, total Ub content correlated with the increase in ATP-dependent proteolysis and in Ub mRNA.

The covalent linkage of Ub to cell proteins is known to mark them for rapid degradation. Therefore, we also measured the muscles content of ubiquitin-protein conjugate in normal and denervated muscle. As shown in Table XIII, the levels of ubiquitinated proteins increased by 158% after denervation for 2 days. A similar increase in ubiquitinated proteins was seen upon fasting of the rats (data not shown) and this difference disappeared upon refeeding the animals for one day. These findings further indicate activation of the ubiquitin dependent process in atrophying muscles.

In the denervated muscle and in fasted animals, there was also found an increase in rate of proteasome synthesis, as indicated by a 2-3 fold increase in mRNA for various subunits of the proteasome (Table XIII). Shown there are mRNA for subunits C-3 and C-9 and in related experiments, a similar increase was seen in mRNA for three other subunits. Thus, the atrophying muscles are increasing levels of multiple components of this degradative pathway.

Discussion

These changes in Ub mRNA following denervation, fasting or refeeding occur in parallel with and appear to be linked to the alterations in overall protein breakdown and in degradation of myofibrillar proteins measured in the incubated muscles. The rise in Ub mRNA seen in the atrophying muscles appears responsible for their increased Ub content (Table XII), which occurred despite the net loss of total muscle protein. Furthermore, the preceding examples demonstrated that these changes in overall proteolysis are due to activation of a nonlysosomal ATP-dependent process and that fasting leads to enhanced ATP-Ub-stimulated proteolysis in soluble extracts of muscle.

Several more recent observations also strongly support the conclusion that the Ub-dependent proteolytic system is enhanced under these conditions. As described herein, it was also observed that the muscles from fasting animals and denervated muscles also showed higher levels of Ub-conjugated proteins and of mRNA encoding the proteasome, which is essential in the breakdown of such ubiquitinated proteins. These results together indicate that the Ub-dependent system in muscle is precisely regulated by contractile activity and food intake. The response to fasting requires adrenal steriods (Kettelhut, I. C. et al., *Diabetes/Metabolism Reviews*, 4:751-772 (1988); Goldberg, A. L. et al., *Federation Proc.*, 39:31-36 (1980)), and glucocorticoids have been found to be necessary for both the increased ATP-dependent proteolysis and the accompanying rise in Ub mRNA in fasting.

The changes shown here in Ub mRNA levels parallel exactly the changes in overall protein degradation and in the breakdown of myofibrillar proteins, both of which were shown in the preceding examples to occur by an ATP-dependent nonlysosomal process. The present data thus suggest a more general role for this system in the degradation of normal muscle proteins, including probably the long-lived myofibrillar components.

The polyUb gene seems to be an example of a gene that is specifically induced in atrophying muscles. In fasting or denervation atrophy, when muscle mass and overall RNA are decreasing, the levels of polyUb mRNA and Ub concentration rose. In contrast, the levels of the Ub-extension mRNA did not change or may have fallen, as would be expected since this transcript is involved in production of new ribosomes (Finley, D. et al., *Nature*, 338:394-401 (1989); Redman, K. and Rechsteiner, M., *Nature*, 338:438-440 (1989)). Thus, poly Ub mRNA levels and Ub production seem to be regulated inversely to total RNA or to mRNA for the Ub-extension protein.

Of particular physiological interest is the finding that the increase in Ub mRNA (and presumably, therefore, in Ub) is restricted to striated muscle. Such changes also occur in the rat heart, which in fasting undergoes considerable weight loss. These findings suggest that ATP-dependent proteolysis also rises in cardiac muscle under such conditions, presumably by similar mechanisms as in skeletal muscle, although systematic studies have not been reported. The absence of any change in Ub levels in testes or brain was anticipated, since the protein content and size of these organs are maintained during a fast. However, it is noteworthy that levels of Ub mRNA did not change in liver, in which overall proteolysis clearly rises in low insulin states by a lysosomal autophagic mechanism (Dice, J. F., *FASEB J.*, 1:349–356 (1987); Lardeux, B. R. and Mortimore, G. F., *J. Biol. Chem.*, 262:14514–14519 (1987); Mortimore, G. E. et al., *Diabetes/Metabolism Reviews*, 5:49–70 (1989)). These findings thus suggest that the relative importance of different proteolytic processes differ between tissues and that the ATP-Ub-dependent pathway is of special significance in striated muscle, particularly in catabolic states.

TABLE XII

EFFECTS OF DENERVATION AND FASTING ON UBIQUITIN LEVELS IN RAT SKELETAL MUSCLES

| Muscle | Total Protein (mg/muscle) | Total Ubiquitin (pmol/muscle) | Total Ubiquitin (pmol/mg protein) |
|---|---|---|---|
| Soleus | | | |
| Innervated | 3.5 ± 0.4 | 89 ± 5 | 27 ± 2 |
| Denervated | 2.7 ± 0.2 | 137 ± 12 | 51 ± 2 |
| Difference | −0.8 ± 0.3** | +47 ± 11** | +24 ± 3** |
| % Change | −23% | +53% | +91% |
| EDL | | | |
| Fed | 4.5 ± 0.3 | 71 ± 6 | 16 ± 1 |
| Fasted 2 days | 3.1 ± 0.4 | 79 ± 7 | 26 ± 2 |
| Difference | −1.4 ± 0.5* | +7 ± 9 | +10 ± 2** |
| % Change | −32% | +10% | +63% |

Values are the means ± SEM for extensor digitorum longus (EDL) muscles from four fed or fasted animals and for seven paired soleus muscles two days following section of one of the sciatic nerves. Significance difference, *$p < 0.05$, **$p < 0.01$.

TABLE XIII

EFFECTS OF DENERVATION FOR 2 DAYS ON ATP-DEPENDENT PROTEOLYSIS AND LEVELS OF UBIQUITIN AND UBIQUITIN-CONJUGATES IN RAT SOLEUS

| | ATP-Dependent Proteolysis (pmol tyr/mg/2h) | Free Ubiquitin | Ubiquitin Conjugates (pmol Ub/mg protein) | Total Ubiquitin |
|---|---|---|---|---|
| Control | 63.0 ± 11 | 17.0 ± 1.3 | 10.0 ± 0.7 | 27 ± 1.9 |
| Denervated | 201.0 ± 17 | 25.0 ± 1.2 | 26.0 ± 1.3 | 51 ± 2.2 |
| % Increase | 232% * | 52% * | 158% * | 92% * |

* Means ± S.E.M. of 7. * $p < .01$.

TABLE XIV

DENERVATION OF THE RAT GASTROCNEMIUS FOR 4 DAYS INCREASES mRNA CONTENT FOR UBIQUITIN, AND ALSO TWO PROTEASOME SUBUNITS

| mRNA | Control (Arbitrary Units) | Denervated (Arbitrary Units) |
|---|---|---|
| Polyubiquitin | 36.4 ± 3.58 | 63.4 ± 3.63** |
| C3-Proteasome Subunit | 32.6 ± 4.41 | 67.2 ± 4.29** |
| C9-Proteasome Subunit | 25.2 ± 7.79 | 74.4 ± 7.78* |

**($p > 0.01$)
*($p < 0.05$)

TABLE XV

INJECTIONS OF *E. COLI* ENDOTOXIN (LPS) RAPIDLY STIMULATE PROTEIN BREAKDOWN SIMILARLY IN RAT EXTENSOR DIGITORUM LONGUS MUSCLE

| Injection | Proteolysis (nmol tyrosine/mg/2h) Saline | Treated | Difference |
|---|---|---|---|
| LPS | 0.214 ± 0.013 | 0.280 ± 0.015 | +31% $P < 0.01$ |

INJECTION OF ENDOTOXIN (LPS) ACTIVATES THE ATP-DEPENDENT PATHWAY OF PROTEIN BREAKDOWN IN RAT MUSCLES

| Addition | Proteolysis (nmol tyrosine/mg/2h) | | |
|---|---|---|---|
| Non Lysosomal Proteolysis* | 0.145 ± 0.009 | 0.190 ± 0.017 | +31% $P < 0.05$ |
| After ATP depletion | 0.094 ± 0.004 | 0.102 ± 0.004 | NS |
| (ATP-dependent component) | 0.051 ± 0.009 | 0.088 ± 0.014 | +73% $P < 0.05$ |

*Lysosomal and Ca2+-dependent processes are not altered under these conditions. Young (60–80 g) male Charles River rats were given free access to water and Purina Lab Chow. They were injected between 7 and 8 A.M. with sterile saline (0.9% NaCl) and *E. coli* LPS (40 mg/100 g body weight dissolved in saline, and killed 6 hours later.

Activation of Protein Breakdown During Systemic Infections

One other condition where muscle protein breakdown increases markedly is during systemic infections of bacterial, viral or parasitic origin. Patients with sepsis, which often follows traumatic injuries, tend to be in marked negative nitrogen balance due mainly to accelerated muscle pro breakdown. This response is associated with fever and is part of the body's acute phase response. It can be mimicked in animals by injection of endotoxin or live bacteria (Goldberg, A. L. et al., *J. Clin. Inv.* (1989)). A variety of experiments indicate this enhancement of proteolysis is signaled by circulating factors released by activated macrophages. As shown in Table XV, 6 hours after endotoxin injection, animals were killed and their leg muscles studied in vitro. The EDL showed a rapid increase in overall protein breakdown. This response was not due to the lysosomal or calcium activated proteases. When the ATP-dependent degradative system was measured, it had increased by 70% and could account for the overall increase of protein breakdown in the animals. Treatment of the rats with endotoxin also caused 2-3 fold increase in the levels of polyUb mRNA in these muscles within 6–7 hours. This rise in polyUb mRNA which resembles the response seen in fasting or denervation, was not seen in other tissues. Northern analysis of gastrocnemius muscles, excised shows after injection of *E. coli* endotoxin (40 μg/100 g body weight), using cDNA probes of polyubiquitin genes also showed induction of ubiquitin in RNA (data not shown). These findings thus indicate a common biochemical program in muscle leading to enhanced protein breakdown in these three catabolic states and others, including cancer cachexia as induced in rats carrying Yochida hepatoma in ascities and in rats with metabolic acidosis induced by injection of NH4Cl (data not shown).

EXAMPLE 7

Isolation of the 40 kDa Inhibitor of the Proteasome

Materials and Methods

DEAE-cellulose (DE-52), CM-cellulose (CM-52), and phosphocellulose (P11) were obtained from Whatman. Ub-conjugating enzymes (E1, E2 and E3) were isolated using Ub-sepharose affinity column chromatography (Hershko, A. et al., *J. Biol. Chem.*, 258:8206–8214 (1983)), and were used to prepare Ub-$^{125}$I-lysozyme conjugates (Hershko, A. and H. Heller, *Biochem. Biophys. Res. Comm.* 128:1079–1086 (1985)). All other materials used were as described in the previous examples.

Purifications

Rabbit reticulocytes induced by phenylhydrazine injection were prepared (as described previously or purchased from Green Hectares (Oregon, Wis.). They were depleted of ATP by incubation with 2,4-dinitrophenol and 2-deoxyglucose as described (Ciechanover, A. et al., *Biochem. Biophys. Res. Comm.* 81:1100–1105 (1978)). Lysates were then prepared and subjected to DE-52 chromatography. The protein eluted with 0.5M KCl (Hershko, A. et al., *J. Biol. Chem.*, 258:8206–8214 (1983)) was concentrated using ammonium sulfate to 80% saturation, centrifuged at 10,000×g for 20 minutes, and suspended in 20 mM Tris-HCl (pH 7.6), 1 mM DTT (buffer A). Following extensive dialysis against the same buffer, the protein (fraction II) was either stored at −80° C. in 0.5 mM ATP or fractionated further.

Fraction II (∼200 mg) was applied to a Ub-sepharose column, and the Ub-conjugating enzymes were specifically eluted (Hershko, A. et al., *J. Biol. Chem.*, 258:8206–8214 (1983)) and used in making Ub-lysozyme (Hershko, A. and H. Heller, *Biochem. Biophys. Res. Comm.* 128:1079–1086 (1985)). The unadsorbed fraction was brought to 38% saturation using ammonium sulfate and mixed for 20 minutes, as described by Ganoth et al. (Ganoth, D. et al., *J. Biol. Chem.* 263:12412–12419 (1988)). The precipitated proteins were collected by centrifugation at 10,000×g for 15 minutes. The pellet was resuspended in buffer A and brought again to 38% saturation with ammonium sulfate. The precipitated material was collected as above and then suspended in buffer A containing 10% glycerol. After dialysis against this buffer, the 0–38% pellet was chromatographed on a Mono-Q anion exchange column equilibrated with buffer A containing 10% glycerol. The protein was eluted using a 60 ml linear NaCl gradient from 20 to 400 mM. Fractions which inhibited the peptidase activity of the proteasome were pooled, concentrated, and then chromatographed on a Superose 6 (HR 10/30) gel filtration column equilibrated in buffer A containing 100 mM NaCl and 0.2 mM ATP. The column was run at a flow rate of 0.2 ml/min, and 1 ml fractions were collected. In certain experiments to analyze for CF-2 ability (see Results), further purification of the inhibitor was achieved by a second more narrow Mono-Q chromatographic gradient (from 50 to 300 mM NaCl), which yielded a sharp peak of inhibitor where only the 40 kDa band was visible after SDS-PAGE and Coomasie staining. Fractions with inhibitory activity against the proteasome were pooled and dialyzed against buffer B which contained 20 mM KH$_2$PO$_4$ (pH 6.5), 10% glycerol, 1 mM DTT and 1 mM ATP. The sample was then applied to a 2 ml phosphocellulose column equilibrated in buffer B. The column was washed with 4 ml of this buffer, followed by 4 ml of this buffer, followed by 4 ml of buffer B containing either 20, 50, 100, 400 or 600 mM NaCl.

To obtain partially pure CF-1, the mono Q fractions that eluted from 100 to 240 mM NaCl were pooled, concentrated to 1 ml and applied to a superose 6 column equilibrated in buffer A containing 100 mM NaCl and 0.2 mM ATP. The fractions eluting at approximately 600 kDa were used as the CF-1 containing fraction.

The proteasome was isolated from the supernatants of the two 38% ammonium sulfate precipitations. The supernatants were brought to 80% saturation with ammonium sulfate and mixed for 20 minutes. The precipitated protein was collected by centrifugation, resuspended in buffer A, and dialized extensively against this buffer. The proteasome was isolated by Mono-Q anion exchange chromatography followed by gel filtration on superose 6 as described previously (Driscoll, J. and A. L. Goldberg, *Proc. Natl. Acad. Sci., USA* 86: 789–791 (1989)).

The 1,500 kDa proteolytic complex was generated by incubating reticulocyte fraction II at 37° C. for 30 minutes in the presence of 2 mM ATP, 5 mM MgCl$_2$ in 50 mM Tris-HCl (pH 7.6). After precipitation with ammonium sulfate to 38% saturation, the pellet was collected at 10,000×g for 10 minutes, suspended in buffer A, and isolated by Mono Q anion exchange and superose 6 chromatography.

Assays

Inhibition of the proteasome was measured by preincubating individual column fractions with the proteasome in the presence of 1 mM ATP at 37° C. for 10 minutes. After preincubation, the reaction tubes were placed on ice, and either $^{125}$I-lysozyme or Suc-LLVY-MCA was added. Reactions were carried out at 37° C. for 60 minutes with $^{125}$I-lysozyme or 10 minutes with Suc-LLVY-MCA. Protein hydrolysis was assayed by measuring production of radioactivity soluble in 10% trichloroacetic acid, and peptide hydrolysis by the release of methylcoumaryl-7-amide (Driscoll, J. and A. L. Goldberg, *Proc. Natl. Acad. Sci., USA* 86:789–791 (1989)). Degradation of Ub-conjugated $^{125}$-I-lysozyme was assayed at 27° C. for 60 minutes. Reactions contained either 5 mM EDTA or 2 mM ATP and 5 mM MgCl$_2$ and were terminated by adding 10% trichloroactic acid.

Results

Isolation of the Inhibitor

To understand how the proteasome is regulated in vivo and how it functions in the Ub-conjugate-degrading complex, we attempted to isolate factors which influence its activity. Reticulocyte fraction II was separated using ammonium sulfate into fractions which precipitated with either 0–38% or 40–80%. The latter fraction was used to isolated proteasomes. These particles (obtained in this way from ATP-depleted reticulocytes) showed appreciable activity against $^{125}$I-lysozyme and Suc-LLVY-MCA which was indepedent of ATP (Eytan, E. et al., *Proc. Natl. Acad. Sci., USA* 86:7751–7755 (1989); Driscoll, J. and A. L. Goldberg, *J. Biol. Chem.* 265:4789–4782 (1990)). Neither the proteasome nor the 0–38% fraction showed significant activity against Ub-conjugated $^{125}$I-lysozyme (Eytan, E. et al., *Proc. Natl. Acad. Sci., USA* 86:7751–7755 (1989); Driscoll, J. and A. L. Goldberg, *J. Biol. Chem.* 265:4789–4792 (1990)). However, as reported previously, ATP-dependent degradation of the ubiquitinated lysozyme was observed after the proteasome and the 0–38% fraction were preincubated together in the presence of ATP (data not shown).

The 0–38% precipitated material then was separated using Mono-Q anion exchange and each fraction assayed for its ability to influence the proteasome activity against Suc-LLVY-MCA or $^{125}$I-lysozyme. Column fractions were preincubated with the proteasome for 10 minutes and then either substrate was added. None of the column fractions by itself showed significant hydrolytic activity did not affect proteasome activity, a peak of inhibitory activity was eluted around 240 to 280 mM NaCl. It significantly decreased its proteolytic activity against both substrates. Moreover, hydrolysis of lysozyme and the peptide was inhibited to a similar extent.

To purify the inhibitory activity further, the active fractions were pooled and chromatographed by gel filtration. The inhibotr eluted as a sharp peak with an apparent molecular weight of ~100–150 kDa.

The active fractions were then pooled and assayed for their ability to inhibit the proteasomes substrate hydrolyzing activities. With increasing inhibitor concentration, proteasome activity decreased in a linear manner with both $^{125}$I-lysozyme and Suc-LLVY-MCA as substrates, although the degree of the inhibition was highly variable between preparations.

The Inhibitor is a Component of the 1,500 kDa Proteolytic Complex

Like the inhibitor, one component of the 1,500 kDa proteolytic complex (CF-2) has been reported to have a molecular weight of ~250 kDa. To test if the inhibitor corresponds to CF-2, the inhibitor obtained by gel filtration was subject to phosphocellulose chromatography. Eytan et al. had noted that CF-2 has little affinity for phosphocellulose and eluted with less than 100 mM NaCl 11. Accordingly, the inhibitory activity was recovered in the flow through and 20 mM NaCl eluate (i.e., in the region where CF-2 activity was reported). Individual phosphocellulose fractions were then assayed for their ability to reconstitute degradation of ubiquitinated lysozyme. Individually or combined, the proteasome and CF-1 containing fraction did not support rapid breakdown of ubiquitinated lysozyme. However, when this mixture was combined with the peak of the inhibitor activity, the rate of Ub $^{125}$I-lysozyme degradation increased sharply. No other phosphocellulose fractions stimulated this process.

These results suggest strongly that the inhibitor corresponds to CF-2 and thus is essential for hydrolysis of Ub-ligated proteins. One unusual property of CF-2 is that it is quite labile upon heating to 42° C., but is stabilized by ATP (Ganoth, D. et al., *J. Biol. Chem.* 263:12412–12419 (1988)). To test further if the inhibitor of the proteasome corresponds to CF-2, the purified inhibitor was preincubated at 42° C. with or without ATP or the nonhydrolyzable analog, AMPPNP. The proteasome was added and after 10 minutes, peptidase activity was assayed. The degree of inhibition decreased rapidly during preincubation without nucleotide added. The presence of either ATP or AMPPNP prevented this loss of activity. Furthermore, the ability of this material to reconstitute degradation of Ub-conjugated lysozyme also decreased rapidly during incubation at 42° C., and the addition of ATP or AMPPNP (not shown) prevented this activation. Since the inhibition and reconstitution of Ub-conjugate degradation showed similar inactivation kinetics and were stablized similarly by ATP, these two functions probably reside in a single molecule which appears to bind ATP.

Although ATP stabilizes the inhibitory factor, it is not essential for inhibition of the proteasome. After preincubation of the inhibitor with proteasome for up to 20 minutes with or without ATP, a similar degree of inhibition was observed. Nevertheless, because of the stabilization by ATP, this nucleotide was routinely added to all incubations.

When analyzed by SDS-PAGE, the inhibitor preparations showed a major band of ~40 kDa. To test whether this 40 kDa subunit corresponded to any subunit of the 1,500 kDa complex, the 1,500 kDa complex was formed by incubation of fraction II with $Mg^{2+}$-ATP and isolated by anion exchange and gel filtration chromatography. SDS-PAGE of these active fractions indicated many polypeptides similar to those previously reported for this complex (Hough, R. et al., *J. Biol. Chem.* 262:8303–8313 (1987); Ganoth, D. et al., *J. Biol. Chem.* 263:12412–12419 (1988); Eytan, E. et al., *Proc. Natl. Acad. Sci. USA* 86:7751–7755 (1989)). However, a readily apparent band of 40 kDa was evident in this fraction. To further address the question of proteins associated with the proteasome, fraction II wsa immunoprecipitated using and anti-proteasome monoclonal antibody and analyzed by SDS-PAGE. Ub-conjugate degrading activity had previously been shown to be removed upon immunoprecipitation of fraction II (Matthews, W. et al., *Proc. Natl. Acad. Sci., USA* 86:2597–2601 (1989)). Upon SDS-PAGE of the immunoprecipitates, we observed the characteristic set of proteasome subunits ranging from 20 to 34 kDA, along with other higher molecular weight bands. Importantly, a 40 kDa band, similar to that of the inhibitor and similar to that seen in the partially purified complex was detected in the immunoprecipitate.

Equivalents

Those skilled in the art will recognize, or be able to ascertain, using no more than routine experimentation, many equivalents to the specific embodiments of the invention described herein. Such equivalents are intended to be encompassed by the following claims.

I claim:

1. Isolated component of the Ubiquitin-Conjugate-Degrading-Enzyme, said isolated component selected from the group consisting of:
  (a) multipain of approximately 500 kDa, which has a proteolytic activity that preferentially cleaves ubiquitinated proteins in an ATP-dependent manner; and
  (b) multipain-proteasome complex of approximately 1500 kDa, comprising the multipain of (a) and the proteasome, said complex which has a proteolytic activity that cleaves ubiquitinated and non-ubiquitinated proteins in an ATP-dependent manner.

2. The isolated component of claim 1 which is isolated from muscle.

* * * * *